United States Patent
Adams et al.

(10) Patent No.: US 12,327,614 B2
(45) Date of Patent: Jun. 10, 2025

(54) MULTI-DOMAIN PROTEINS WITH INCREASED NATIVE STATE COLLOIDAL STABILITY

(71) Applicant: UCB Biopharma SRL, Brussels (BE)

(72) Inventors: Ralph Adams, Slough (GB); James Heads, Slough (GB); Sebastian Kelm, Slough (GB); Alastair David Griffiths Lawson, Slough (GB)

(73) Assignee: UCB BIOPHARMA SRL, Brussels (BE)

( * ) Notice: Subject to any disclaimer, the term of this patent is extended or adjusted under 35 U.S.C. 154(b) by 1203 days.

(21) Appl. No.: 16/972,458

(22) PCT Filed: Jun. 5, 2019

(86) PCT No.: PCT/EP2019/064635
§ 371 (c)(1),
(2) Date: Dec. 4, 2020

(87) PCT Pub. No.: WO2019/234094
PCT Pub. Date: Dec. 12, 2019

(65) Prior Publication Data
US 2021/0166780 A1 Jun. 3, 2021

(30) Foreign Application Priority Data
Jun. 7, 2018 (GB) .................................... 1809341

(51) Int. Cl.
*G16B 15/20* (2019.01)
*C07K 16/00* (2006.01)
(Continued)

(52) U.S. Cl.
CPC .............. *G16B 15/20* (2019.02); *C07K 16/00* (2013.01); *G16B 15/00* (2019.02); *G16B 30/00* (2019.02);
(Continued)

(58) Field of Classification Search
CPC ........ G16B 15/20; G16B 15/00; G16B 30/00; G16B 40/00; G16B 5/00; G16B 20/50;
(Continued)

(56) References Cited

U.S. PATENT DOCUMENTS

| | | | | |
|---|---|---|---|---|
| 2004/0110226 | A1* | 6/2004 | Lazar | C07K 16/32 435/7.1 |
| 2006/0271306 | A1* | 11/2006 | Dobson | G16B 15/00 702/19 |
| 2011/0257104 | A1* | 10/2011 | Chennamsetty | C07K 14/71 530/402 |

FOREIGN PATENT DOCUMENTS

| | | |
|---|---|---|
| EP | 2 233 500 A1 | 9/2010 |
| WO | 2008/020827 A2 | 2/2008 |

(Continued)

OTHER PUBLICATIONS

Spassov, Velin Z., Andrej D. Karshikoff, and Rudolf Ladenstein. "The optimization of protein-solvent interactions: Thermostability and the role of hydrophobic and electrostatic interactions." Protein science 4.8 (1995): 1516-1527. (Year: 1995).*

(Continued)

*Primary Examiner* — Jesse P Frumkin
(74) *Attorney, Agent, or Firm* — MEDLER FERRO WOODHOUSE & MILLS PLLC

(57) ABSTRACT

The present invention provides a method for generation of multi-domain proteins, more particular antibodies, with an improved native state colloidal stability. The present disclosure provides a method of producing an IgG1 or IgG4 antibody with an improved colloidal stability comprising, in embodiments: calculating for each domain of said IgG1 or IgG4 antibody the total net charge at a given pH; introducing one or more modifications to the amino acid residues of the constant region of said IgG1 or IgG4 antibody to minimize the charge sign difference between the domains, wherein said one or more modi- (Continued)

fication is, or each are, a substitution of a charged amino acid by a polar (non-charged) amino acid; and producing the modified multi-domain protein with improved colloidal stability at the given pH.

18 Claims, 7 Drawing Sheets

(51) Int. Cl.
    *G16B 15/00*     (2019.01)
    *G16B 30/00*     (2019.01)
    *G16B 40/00*     (2019.01)
    *G16C 20/50*     (2019.01)
    *G16B 5/00*     (2019.01)

(52) U.S. Cl.
    CPC ............. *G16B 40/00* (2019.02); *G16C 20/50* (2019.02); *C07K 2317/52* (2013.01); *C07K 2317/92* (2013.01); *C07K 2317/94* (2013.01); *G16B 5/00* (2019.02)

(58) Field of Classification Search
    CPC ............... C07K 16/00; C07K 2317/92; C07K 2317/94; C07K 2317/52; G16C 20/50
    See application file for complete search history.

(56) References Cited

FOREIGN PATENT DOCUMENTS

WO      WO-2009155518 A1 * 12/2009 ....... A61K 39/39591
WO      2011/122011 A2    10/2011

OTHER PUBLICATIONS

International Search Report issued Nov. 19, 2019, in International Appl. No. PCT/EP2019/064635.
Burnsteiner et al., "Structure Based Descriptors for the Estimation of Colloidal Interactions and Protein Aggregation Propensities," PLOS ONE 8(4):e59797 (2013).
Chennamsetty et al., "Design of Therapeutic Proteins with Enhanced Stability," National Academy of Sciences 106(29):11937-11942 (2009).
Kuhn et al., "Improved Solution-State Properties of Monoclonal Antibodies by Targeted Mutations," Journal of Physical Chemistry Part B 121(48):10818-10827 (2017).
Perchiacca et al., "Optimal charged mutations in the complementarity-determining regions that prevent domain antibody aggregation are dependent on the antibody scaffold," Protein Engineering, Design & Selection 27(2):29-39 (2014).
Rouet et al., "Stability engineering of the human antibody repertoire," FEBS Letters 588(2):269-277 (2013).
Tiller et al., "Advances in Antibody Design," Annual Review of Biomedical Engineering 17(1):191-216 (2015).
Yadav et al., "The Influence of Charge Distribution on Self-Association and Viscosity Behavior of Monoclonal Antibody Solutions," Molecular Pharmaceutics, 9(4):791-802 (2012).

* cited by examiner

MULTI-DOMAIN PROTEINS WITH INCREASED NATIVE STATE COLLOIDAL STABILITY

The present invention relates to native state colloidal stability of multi-domain proteins and provides methods for optimizing such stability.

BACKGROUND

The stability of bio-pharmaceuticals formulations depends on various stability parameters like colloidal and chemical stability, among others. Colloidal stability of multi-domain protein solutions is an important consideration in formulation development of therapeutics or commercial reagents. Such stability can be described otherwise as the propensity of the natively folded protein to precipitate in a solution. Solution pH and ionic strength are two key factors that affect the native state colloidal stability of protein solutions.

Typically an isoelectric point and net charge of a multi-domain protein is measured when investigating the charge and colloidal stability of a molecule. The hydrophobicity of a protein is also often considered when estimating aggregation probability. The methodology described in US2011/0257104, for example, is predominantly based on hydrophobic patches. Many of the existing methods are usually validated using heat and other stress conditions. Such stresses partially unfold the molecule exposing the hydrophobic core. As the molecule is no longer in its native state in these studies predictions of colloidal aggregation propensity is significantly compromised, and often biased towards a hydrophobic model.

Current experimental approaches for evaluating the solubility of protein therapeutics are based on salt (ammonium sulfate) induced precipitation (Banks et al, 2012) or PEG-induced protein precipitation (Gibson et al, 2011). PEG induced precipitation assays are more often used to study colloidal interactions as ammonium sulphate precipitation requires the addition of high salt concentrations which can perturb native electrostatic interactions between protein molecules.

There exists a need for new methods and systems for predicting protein aggregation propensity and providing guidance of how to modify a multi-domain protein to decrease its propensity to aggregate. Such methods and systems would provide benefits in the identification and selection of protein formulations that minimize aggregation and extend long-term stability and the identification of protein variants with the lowest tendency to aggregate.

The present invention addresses these needs. The methods of the present invention allow to predict the colloidal aggregation propensity of multi-domain molecules based on the frequency of charge interactions between the domains of native folded molecules.

The present invention provides a linear sequence and homology model based method to predict probability of native state colloidal aggregation propensity from amino acid sequence of a multi-domain protein. Furthermore, the method of the present invention omits opposite charge pairs within a defined distance of each other improving robustness of aggregation prediction.

SUMMARY OF THE INVENTION

The present invention provides a method of producing a multi-domain protein with an improved colloidal stability comprising:

calculating for each domain of said protein of interest the total net charge at a given pH;

introducing one or more modifications to the charged amino acid residues of said protein to minimize the charge sign difference between the domains;

producing the modified multi-domain protein with improved colloidal stability at the given pH.

Optionally said method comprises additional steps of calculating the hydrophobicity of the domains of said protein, and introducing one or more modifications to the hydrophobic residues to decrease the hydrophobicity of the domains.

The present invention provides a method of selecting and producing one or more multi-domain proteins with improved colloidal stability, comprising:

obtaining two or more of multi-domain protein sequences from a panel of structurally similar multi-domain proteins sequences;

calculating for said two or more multi-domain protein sequences one or more charge scores for each of the domains;

selecting one or more multi-domain protein sequences from said two or more multi-domain protein sequences with the desired range of charge scores; and producing one or more multi-domain proteins using the selected multi-domain protein sequences.

The present invention further provides a method of screening for multi-domain proteins with improved colloidal stability, comprising:

selecting a multi-domain protein of interest;

generating a set of sequences with one or more modifications to the charged amino acid residues of said protein to minimize the charge sign difference between the domains;

calculating for each generated modified sequences a one or more charge scores for each of the domains of said protein at a given pH;

selecting sequences with the desired range of the charge scores;

producing multi-domain proteins using selected sequences;

measuring the colloidal stability of the produced proteins; and identifying proteins with desired level of colloidal stability at the given pH.

The present invention further provides a system for predicting colloidal stability of a multi-domain protein, said system comprising a receiver configured to receive, one or more protein sequences;

a charge score estimator configured to calculate the net charge per domain of said one or more protein sequences;

a colloidal stability estimator configured to calculate one or more predictive stability scores at a given pH; and an output device configured to display the probability of colloidal stability calculated by the colloidal stability estimator.

The present invention also provides modified IgG antibodies with an improved colloidal stability that have been obtained using the methods described herein.

BRIEF DESCRIPTION OF THE DRAWINGS

The present invention is described below by reference to the following drawings, in which.

DETAILED DESCRIPTION OF THE INVENTION

Abbreviations

Figure 1:
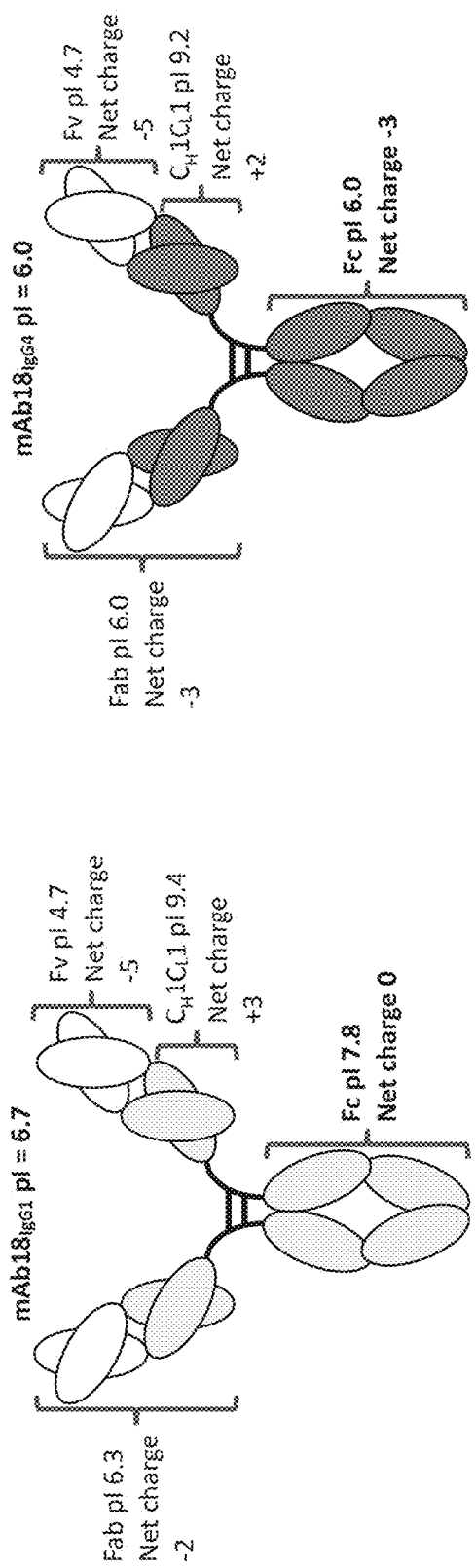
FIG. 1 is a schematic drawing showing mAb 18 as an IgG1 (light grey constant domains) and IgG4 (dark grey constant domains) isotypes. Isoelectric points (pI) calculated using MPCT, net charge calculated by subtracting sum of basic residues from the sum of acidic residues at pH 7.4 (charge calculation may be modified).

The following abbreviations are used herein: mAb, monoclonal antibody; PPI, protein-protein interactions; IgG, immunoglobulin G; Fab, fragment antigen binding; Fc, fragment crystallizable; Fv, fragment variable; VL, variable domain of a light chain; VH, variable domain of a heavy chain; CH1, first domain in constant portion of a heavy chain; CH2, second domain in constant portion of a heavy chain; CH3, third domain in constant portion of a heavy chain; PBS: phosphate buffered saline.

TABLE 1

Amino acids abbreviations

| Abbreviation | 1 letter abbreviation | Amino acid name |
|---|---|---|
| Ala | A | Alanine |
| Arg | R | Arginine |
| Asn | N | Asparagine |
| Asp | D | Aspartic acid |
| Cys | C | Cysteine |
| Gln | Q | Glutamine |
| Glu | E | Glutamic acid |
| Gly | G | Glycine |
| His | H | Histidine |
| Ile | I | Isoleucine |
| Leu | L | Leucine |
| Lys | K | Lysine |
| Met | M | Methionine |
| Phe | F | Phenylalanine |
| Pro | P | Proline |
| Pyl | O | Pyrrolysine |
| Ser | S | Serine |
| Sec | U | Selenocysteine |
| Thr | T | Threonine |
| Trp | W | Tryptophan |
| Tyr | Y | Tyrosine |
| Val | V | Valine |

Definitions

The following definitions are used throughout the description.

The terms "colloidal stability" or "native state colloidal stability" or "stability" used herein refer to the stability of a natively folded protein in solution. In particular the terms refer to the ability of the natively folded protein to resist flocculation or aggregation and exhibit a long shelf-life. The "colloidal stability" will depend upon the balance of the repulsive and attractive forces that exist between particles in a solution. In particular the term "improved colloidal stability" or "improved stability" means an increase in stability of the protein solution, where the protein particles are less prone to aggregate. Special methods for determining the colloidal stability of liquids containing a biopolymer, especially proteins, are methods which determine the size of the biopolymer or the opalescence/turbidity of the solution. Typical analytical assays are size exclusion chromatography (SEC), SDS-PAGE, photo correlation spectroscopy (PCS), particle counting methods like light-obscuration or imaging methods (e.g. MFI™-method).

The term "pKa" is defined as the negative logarithm of the ionization constant $K_a$ of an acid ($pK_a = -_{10}\log K_a$). The determination of the ionization constant Ka and its definition is explained in "Physical Chemistry", F. Daniels and R. Alberty, Second Edition, 1961, John Wiley and Sons, Inc., pages 364, 365, 428-430.

The term "pI" or "isoelectric point" is the pH at which there is an equal number of positive and negative charges in a molecule so that the molecule carries no net charge. The pI of a protein can be determined by, for example, isoelectric focusing, or similar methods.

The term "salt bridge" used herein refers to a link between electrically charged acidic and basic groups, especially on different parts of a large molecule such as a protein. The salt bridge most often arises from the anionic carboxylate ($RCOO^-$) of either aspartic acid or glutamic amino acid and the cationic ammonium ($RNH^{3+}$) from lysine or the guanidinium ($RNHC(NH_2)^{2+}$) of arginine. Although these are the most common, other residues with ionizable side chains such as histidine, tyrosine, and serine can also participate in salt bridge formation, depending on outside factors perturbing their pKa's.

The term "accessible surface area" (ASA) or "solvent-accessible surface area" is the surface area of a biomolecule that is accessible to a solvent.

The term "antibody" herein refers to multi-domain antibodies. The term "antibody" includes traditional antibodies as well as antibody derivatives and fragments. In general, the term "antibody" includes any polypeptide that includes at least one constant domain, including, but not limited to, CH1, CH2, CH3 and CH4. Traditional antibody structural units typically comprise a tetramer. Each tetramer is typically composed of two identical pairs of polypeptide chains, each pair having one "light" (L) and one "heavy" (H) chain. Human light chains are classified as kappa and lambda light chains. Each heavy chain is comprised of a heavy chain variable region (abbreviated herein as HCVR or VH) and a heavy chain constant region. The heavy chain constant region of an IgG subclass of immunoglobulins, for example, is comprised of three domains, CHI, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4.

The term "monoclonal antibody" as used herein refers to an antibody obtained from a population of substantially homogeneous antibodies,. Thus, the modifier "monoclonal" indicates the character of the antibody as not being a mixture of different antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences.

By "variable region" as used herein is meant the region of an immunoglobulin that comprises one or more Ig domains substantially encoded by any of the V.kappa., V.lamda., and/or VH genes that make up the kappa, lambda, and heavy chain immunoglobulin genetic loci respectively. The terms "variable" or "variable region" refer to the fact that certain segments of the variable region differ extensively in sequence among antibodies. Variability within the variable region is not evenly distributed. Instead, the V regions consist of relatively invariant stretches called framework regions (FRs) of 15-30 amino acids separated by shorter regions of extreme variability called "hypervariable regions" that are each 9-15 amino acids long or longer. The hypervariable region generally encompasses amino acid residues from about amino acid residues 24-34 (LCDR1; "L" denotes light chain), 50-56 (LCDR2) and 89-97 (LCDR3) in the light chain variable region and around about 31-35B (HCDR1; "H" denotes heavy chain), 50-65 (HCDR2), and 95-102 (HCDR3) in the heavy chain variable region; (Kabat et al., 1991).

The terms "Fc", "Fc region" as used herein refers to the constant region of an antibody excluding the first constant region immunoglobulin domain. Thus Fc refers to the last two constant region immunoglobulin domains of IgA, IgD, and IgG, and the last three constant region immunoglobulin domains of IgE and IgM, and the flexible hinge N-terminal to these domains. Although the boundaries of the Fc region may vary, the human IgG heavy chain Fc region is usually defined to comprise residues C226 or P230 to its carboxyl-terminus, wherein the numbering is according to the EU index as in Kabat. Fc may refer to this region in isolation, or this region in the context of an antibody, antibody fragment, or Fc fusion. An Fc may be an antibody, Fc fusion, or an protein or protein domain that comprises Fc. Particularly preferred are Fc variants, which are non-naturally occurring variants of an Fc.

The terms "Fv domain" or "Fv region" refer to The amino-terminal portion of each light and heavy chains a variable region of about 100 or more amino acids primarily responsible for antigen recognition. In the variable region, three loops are gathered for each of the V domains of the heavy chain and light chain to form an antigen-binding site. Each of the loops is referred to as a complementarity-determining region (hereinafter referred to as a "CDR"), in which the variation in the amino acid sequence is most significant.

By "Fab" or "Fab region" as used herein is meant the polypeptide that comprises the VH, CH1 VL, and CL immunoglobulin domains. Fab may refer to this region in isolation, or this region in the context of a full length antibody, antibody fragment or Fab fusion protein. By "Fv" or "Fv fragment" or "Fv region" as used herein is meant a polypeptide that comprises the VL and VH domains of a single antibody.

The terms "IgG" or "IgG immunoglobulin" or "immunoglobulin G" or "IgG antibody" as used herein are related to a polypeptide belonging to the class of antibodies that are substantially encoded by immunoglobulin gamma gene. More particular IgG comprises the subclasses or isotypes IgG1, IgG2, IgG3, and IgG4. IgG antibodies are multidomain tetrameric proteins composed of two heavy chains and two light chains. The IgG heavy chain is composed of four immunoglobulin domains linked from N- to C-terminus in the order VH-CH1-CH2-CH3, referring to the heavy chain variable domain, heavy chain constant domain 1, heavy chain constant domain 2, and heavy chain constant domain 3 respectively. The IgG light chain is composed of two immunoglobulin domains linked from N- to C-terminus in the order VL-CL, referring to the light chain variable domain and the light chain constant domain respectively.

As used herein, the term "isotype" refers to the antibody class (e.g., IgG1, IgG2, IgG3, or IgG4 antibody) that is encoded by the heavy chain constant region genes. More particular the term "isotype" refers to IgG antibody classes.

By "IgG subclass modification" or "IgG isotype modification" as used herein is meant an amino acid modification that converts one amino acid of one IgG isotype to the corresponding amino acid in a different, aligned IgG isotype.

The term "modification" used herein refers to any amino acid substitution, insertion, and/or deletion in a polypeptide sequence or to a chemical alteration of an amino acid. The term "amino acid modification" herein means an amino acid substitution, insertion, and/or deletion in a polypeptide sequence. For clarity, unless otherwise noted, the amino acid is any amino acid coded for by DNA, e.g. the 20 amino acids that have codons in DNA and RNA.

The term "amino acid substitution" or "substitution" or "amino acid replacement" herein means replacement of an amino acid at a particular position in a parent polypeptide sequence with a different amino acid. In particular, in some embodiments, the substitution is to an amino acid that is not naturally occurring at the particular position, either not naturally occurring within the organism or in any organism.

By "amino acid insertion" or "insertion" as used herein is meant the addition of an amino acid sequence at a particular position in a parent polypeptide sequence.

By "amino acid deletion" or "deletion" as used herein is meant the removal of an amino acid sequence at a particular position in a parent polypeptide sequence.

As used herein, the term "protein" herein is meant at least two covalently attached amino acids, which includes proteins, polypeptides, oligopeptides and peptides. The peptidyl group may comprise naturally occurring amino acids and peptide bonds, or synthetic peptidomimetic structures, i.e. "analogs", such as peptoids (see Simon et al., PNAS USA 89(20):9367 (1992)). The amino acids may either be naturally occurring or synthetic. The variants of the present invention may comprise modifications that include the use of synthetic amino acids incorporated using, for example, the technologies developed by Schultz and colleagues, including but not limited to methods described by Cropp & Shultz, 2004, Trends Genet. 20(12):625-30, Anderson et al., 2004, Proc Natl Acad Sci USA 101 (2):7566-71, Zhang et al., 2003, 303(5656):371-3, and Chin et al., 2003, Science 301(5635):964-7. In addition, polypeptides may include synthetic derivatization of one or more side chains or termini, glycosylation, PEGylation, circular permutation, cyclization, linkers to other molecules, fusion to proteins or protein domains, and addition of peptide tags or labels.

The term "protein domain" or "domain" refers to any identifiable longer contiguous subsequence of a protein that can fold, function and exist independently of the rest of the protein chain or structure. A domain is characterized by a three-dimensional structure and can be often stable and folded independently of other domains. As used herein the term "multi-domain protein" refers to proteins that consist of at least two domains. The term "sequence" in the context of a multi-domain protein refers to the total sequence of all domains of such protein. Such sequence of a multi-domain protein contains sequences of the individual domains of such protein. Each domain a multi-domain protein is encoded by the corresponding amino-acid sequence. Hence the term "sequence" in the context of a domain of a protein refers to the sequence encoding that particular domain.

The term "variant protein" or "protein variant", or "variant" as used herein means a protein that differs from the reference protein by at least one amino acid modification. The term protein variant may refer to the protein itself, a composition comprising the protein, or the amino sequence that encodes it. Preferably, the protein variant has at least one amino acid modification compared to the parent protein, e.g. from about one to about seventy amino acid modifications, and preferably from about one to about five amino acid modifications compared to the parent. As described below, in some embodiments the parent polypeptide, for example an Fc parent polypeptide, is a human wild type sequence, such as the Fc region from IgG1, IgG2, IgG3 or IgG4, although human sequences with variants can also serve as reference proteins. The protein variant sequence herein will preferably possess at least about 80% identity to the reference protein sequence, and most preferably at least about 90% identity, more preferably at least about 95-98-99% identity. Variant protein can refer to the variant protein itself, compositions comprising the protein variant, or the DNA sequence that encodes it.

By "position" as used herein is meant a location in the sequence of a protein. Positions may be numbered sequentially, or according to an established format, for example the EU index for antibody numbering.

The term "amino acid" as used herein refers to one of the 20 naturally occurring amino acids that are coded for by DNA and RNA.

The term "pharmaceutical formulation" refers to preparations which are in such form as to permit the biological activity of the active ingredients to be unequivocally effective, and which contain no additional components which are toxic to the subjects to which the formulation would be administered.

"Pharmaceutically acceptable excipients" (vehicles, additives) are those inert substances that can reasonably be administered to a subject mammal and provide an effective dose of the active ingredient employed. These substances are added to a formulation to stabilize the physical, chemical and biological structure of the antibody. The term also refers to additives that may be needed to attain an isotonic formulation, suitable for the intended mode of administration.

Colloidal Stability

The present invention provides methods for screening and production of multi-domain proteins with increased colloidal stability. Importantly the methods of the present invention have been validated on numerous samples at two biologically relevant pH values without external stress such as heat, shaking or extreme pH values.

The present invention provides a methodology to predict aggregation propensity of proteins comprising multiple domains, such as antibodies, by analyzing the number of charged and hydrophobic residues. In addition distributions of said residues for each domain or subset of domains are taken into account to improve granularity of analysis.

To analyze charged and hydrophobic residue distributions the present invention utilizes a homology model based method to predict the probability of colloidal aggregation propensity from amino acid sequence of a multi-domain protein. Any suitable tool for prediction of 3D structure might be used. Such tools are well-known in the field. An example tool is described in Leem et al, 2016.

Furthermore, the method of the present invention omits opposite charge pairs within a defined distance of each other from the net charge analysis. Additionally, the methods provided herein take into account the number of unpaired charge residues to assess the probability of a charge interaction.

The results provided in examples herein demonstrate that the electrostatic force between domains or subsets of domains of a protein of interest modulates colloidal aggregation in a predictable manner.

Hydrophobicity and Hydrophobicity Scores

Most proteins contain a hydrophobic core of nonpolar amino acid side chains (combined with charged side chains that are neutralized by salt bridges), leaving most of the polar or charged residues on the solvent-exposed protein surface. Exposed hydrophobic residues are energetically unfavorable and are known to promote aggregation events.

The table below illustrates relative hydrophobicity of amino acids, values are normalized so that the most hydrophobic residue is given a value of 100 relative to glycine, which is considered neutral (0 value). The scales were extrapolated to residues which are more hydrophilic than glycine. Monera et al., J. Protein Sci. 1: 319-329 (1995).

TABLE 2

An example of relative hydrophobicity
scores of different amino acids

| Very Hydrophobic pH 7 | |
|---|---|
| Phe | 100 |
| Ile | 99 |
| Trp | 97 |
| Leu | 97 |
| Val | 76 |
| Met | 74 |
| Hydrophobic pH 7 | |
| Tyr | 63 |
| Cys | 49 |
| Ala | 41 |
| Neutral pH 7 | |
| Thr | 13 |
| His | 8 |
| Gly | 0 |
| Ser | −5 |
| Gln | −10 |
| Hydrophilic pH 7 | |
| Arg | −14 |
| Lys | −23 |
| Asn | −28 |
| Glu | −31 |
| Pro | not available |
| Asp | −55 |

Hydrophobicity scores for a sequence or a part of a sequence can be calculated based on any existing scales. Such scores are usually calculated for a part of a sequence and can be an average of the individual scores of each hydrophobic amino acid within that sequence. Typically a hydrophobicity plot for sequence or a protein is constructed. Computation of the hydrophobicity plot requires setting a window size. The computation starts with the first window of amino acids, the average hydrophobicity score of the first window is calculated and plotted as the midpoint of the window. Then the window moves by one amino acid and the average hydrophobicity score of the second window is calculated and plotted as the midpoint of the window. This reiterative process continues until the last window at the end of the sequence. The averages are then plotted on a graph. The y-axis represents the hydrophobicity scores and the x-axis represents the window number or position of the amino acids. When calculating a score or a hydrophobicity plot, each residue's accessible surface area and the distance to surrounding residues is usually taken into account. Examples of hydrophobicity scales have been disclosed in Kyte & Doolittle (1982), Wimley & White (1996), Hessa et al. (2005), Eisenberg & McLachlan (1986), Black & Mould (1990)

Charge and Charge Scores

Protein molecules carry charge according to their amino acid sequence and the aqueous solvent pH they are dissolved in. The functional groups of amino acids and termini determine their charge at a given pH. The protein net charge primarily depends on the number, identity and location of amino acids and the solvent pH. At a certain solvent pH the protein net charge will be zero; this pH is defined as the isoelectric point (pI). At a pH below the pI the molecule will have a net positive charge; a pH above the pI results in a net negative charge.

There are several methods that can be used in the pKa calculations. The first method assumes that all Cysteines are forming Cystines. If there is an uneven number of cysteines in the sequence, a single Cysteine is assumed to be free. The second method assumes that half of the Cysteines present are participating in disulphide linkages (to form Cystine). The third method assumes that none of the Cysteines are participating in disulphide bonds. In order to calculate the pI, a net charge vs. pH plot is generated.

For the purpose of evaluating or calculating the charge of the domains of a protein of interest the acidic amino acid residues (negatively charged) are Asp, Glu and basic amino acid residues (positively charged) are Arg, Lys, His (His is uncharged at neutral pH~7.4). The charge scores are calculated per domain of a multi-domain protein at a given pH. Different approaches can be used to calculate the scores as described further herein. The simplest approach used the counts of the charged residues within a sequence.

Method of Producing Proteins with Improved Colloidal Stability

The present invention provides a method of producing a multi-domain protein with an improved colloidal stability comprising:
calculating for each domain of said protein of interest the total net charge at a given pH;
introducing one or more modifications to the charged amino acid residues of said protein to minimize the charge sign difference between the domains;
producing the modified multi-domain protein with improved colloidal stability at the given pH.

In a particular embodiment the method may additionally comprise the following steps:
calculating the hydrophobicity of the domains of said protein;
introducing one or more modifications to the hydrophobic residues to decrease the hydrophobicity of the domains.

The decrease in charge sign difference between the domains minimizes the level of electrostatic interactions between such domains.

In a specific embodiment the method may additionally comprise a step of calculating for each domain of said protein of interest the number of unpaired charged amino acid residues.

In a particular embodiment one or more modifications to the domains of the protein of interest minimize the number of charged amino acid residues. Such amino acid modifications comprise amino acid deletions, substitutions or insertion that affect the number and the distribution of charges between the domains.

More specifically, said one or more modifications is a replacement of the charged residue by the opposite charged residue. Alternatively, said one or more modifications is a replacement of a charged residue in the proximity of another similar sign charged residue with an oppositely charged residue. A specific example is where said one or more modifications is a replacement of a positively charged residue in the proximity of another positively charged residue into a negatively charged residue. Another example is where said one or more modifications is a replacement of a negatively charged residue in the proximity of another negatively charged residue into a positively charged residue.

In particular the residues are considered to be in close proximity when any atoms from two different similar charged amino acids are within a distance of less than 8, less than 7.5, less than 7, less than 6.5, less than 6, less than 5.5, and less than 5 Å. In a preferred embodiment the residues are considered to be in close proximity when any atoms from two different similar charged amino acids are within a distance of less than 5 Å

In a particular embodiment said one or more modifications additionally minimize the number of unpaired charged residues. A residue is considered unpaired if there is no opposite charged residue present within a particular distance from the residue. More particular if there is no oppositely charged residue is present within a distance of less than 8, less than 7.5, less than 7, less than 6.5, less than 6, less than 5.5, or less than 5 Å. In a preferred embodiment a residue is considered unpaired if there is no opposite charged residue present within a distance of less than 5 Å from the residue. The unpaired residues have more significant effect on charge interactions compared to paired ones.

In yet another embodiment said one or more modifications result in all domains having the same net charge sign at a given pH.

In one embodiment the total net charge at a given pH can be calculated by identifying charged residues in the accessible surface area, and wherein the opposite charged residues located within a particular distance from each other are not taken into the determination of the total charge. More specifically such distance is less than 8, less than 7.5, less than 7, less than 6.5, less than 6, less than 5.5, or less than 5 Å. In a preferred embodiment such distance is less than 5 Å.

In a particular embodiment the total net charge is the sum of unpaired charged residues.

The hydrophobicity can be calculated by identifying the hydrophobic residues in the accessible surface area. In a particular embodiment said hydrophobic surface accessible area corresponds to the sum of the surface of the atoms of the hydrophobic residues.

In one embodiment the hydrophobic residues located within a particular distance from each other can be modified into a charged residue of same charge sign as the net charge sign of the other domains or subset of domains. More specifically such distance between the hydrophobic residues is less than 8, less than 7.5, less than 7, less than 6.5, less than 6, less than 5.5, or less than 5 Å. In a preferred embodiment such distance is less than 5 Å.

In a particular embodiment said charged surface accessible area corresponds to the sum of the surface of the atoms of the charged residues.

In one embodiment said accessible surface area is determined using homology-based modeling using known 3D structures of said domains. The methods using homology-based modeling are well-known to the skilled person and some examples are disclosed above. More specifically the accessible surface area can be determined using a 3D structure data. In particular, the accessible surface area can be determined using X-ray 3D structure data of said domain or said protein of interest.

The one or more modifications can be introduced into the protein of interest to decrease the number of charge clusters. A charge cluster is defined as 3 or more charged residues next to each other in a sequence. Alternatively a charge cluster is a statistically significant charge cluster. Observing a significantly higher count of a charged residue in a set of residues compared to the whole protein structure would be considered to be statistically significant.

When introducing one or more modifications into the protein of interest one or more of the domains can be left unmodified.

Furthermore, when calculating the total net charge or calculating hydrophobicity such calculations can be done for a sub-set of domains instead of each domain individually. This may help to decrease the complexity when applying the methods described herein.

The methods of producing multi-domain proteins with an improved colloidal stability disclosed above can be applied to any multi-domain protein. There is no specific requirements to the number of such domains. Such multi-domain protein must comprise at least two (2) domains. One example of a multi-domain protein is an antibody. More particular the methods described herein can be applied to IgG antibodies.

Methods of Producing IgG Antibodies with Improved Colloidal Stability

In case of IgG antibodies said modification can be a complete domain replacement of an IgG1 domain into IgG4 domain or a replacement of an IgG4 domain into IgG1 domain. For example CH1, CH2 or CH3 domains can be swapped between the isotypes. The one or more modifications can be introduced into a Fc region or a Fv region. Alternatively such modifications can be introduced into CDRs of the antibody.

Negatively charged variable regions paired with IgG1 isotypes increase the probability of charge attraction events. The increased probability of attractive forces would facilitate aggregation events resulting in poorer solubility relative to the IgG4 counterpart. Hence variable region charge affects the colloidal stability of the IgG antibodies and this can be influenced by swapping the negatively charged domains of IgG1 into the corresponding domain(s) of IgG4.

In one embodiment the antibody is an IgG1, and the one or more modifications of IgG are modifications of one or more amino acid residues of the constant region selected from the list consisting of K133, K214, H268, K274, R355, D356, K409 according to Kabat numbering. In an alternative embodiment the antibody is an IgG4, and the one or more modifications of IgG4 are modifications of one or more amino acid residues of the constant region selected from the list consisting of R133, E137, D203, R214, E356, R409, E419 according to Kabat numbering.

In a particular embodiment said protein of interest is IgG1 and said modification is R355Q modification according to Kabat numbering.

In one embodiment the antibody is an IgG1 or IgG4, and the one or more modifications are modifications of one or more amino acid residues selected from the list consisting of residues 131, 133, 137, 138, 196, 199, 203, 214, 234, 268, 274, 296, 327, 330, 331, 355, 356, 358, 409, 419, and 445 of the constant region. The residues that can be modified in the CH1, CH2 and CH3 domains of the constant region are listed in Table 3.

TABLE 3

IgG1 and IgG4 amino acid differences in constant regions.

| Domain | Residue (EU) | IgG1 | IgG4 |
|---|---|---|---|
| CH1 | 131 | Ser (S) | Cys (C) |
| CH1 | 133 | Lys (K) | Arg (R) |
| CH1 | 137 | Gly (G) | Glu (E) |
| CH1 | 138 | Gly (G) | Ser (S) |
| CH1 | 196 | Lys (K) | Gln (Q) |
| CH1 | 199 | Ile (I) | Thr (T) |
| CH1 | 203 | Asn (N) | Asp (D) |
| CH1 | 214 | Lys (K) | Arg (R) |
| CH2 | 234 | Leu (L) | Phe (F) |
| CH2 | 268 | His (H) | Gln (Q) |
| CH2 | 274 | Lys (K) | Gln (Q) |
| CH2 | 296 | Tyr (Y) | Phe (F) |
| CH2 | 327 | Ala (A) | Gly (G) |
| CH2 | 330 | Ala (A) | Ser (S) |
| CH2 | 331 | Pro (P) | Ser (S) |

TABLE 3-continued

IgG1 and IgG4 amino acid differences in constant regions.

| Domain | Residue (EU) | IgG1 | IgG4 |
|---|---|---|---|
| CH3 | 355 | Arg (R) | Gln (Q) |
| CH3 | 356 | Asp (D) | Glu (E) |
| CH3 | 358 | Leu (L) | Met (M) |
| CH3 | 409 | Lys (K) | Arg (R) |
| CH3 | 419 | Gln (Q) | Glu (E) |
| CH3 | 445 | Pro (P) | Leu (L) |

The present invention further provides a method of producing an IgG1 antibody with an improved colloidal stability comprising introducing one or more modifications into constant domains of IgG1, wherein said one or more modifications are modifications of one or more amino acid residues selected from the list consisting of K133, K214, H268, K274, R355, D356, K409 according to Kabat numbering.

More specifically such modification is arginine at the position 355 into any non-charged polar amino acid, more particular such modification is R355Q modification in the CH3 domain according to Kabat numbering. This IgG1 residue mutation to the IgG4 counterpart residue increases solubility and reduces the probability of immunological response.

In an alternative embodiment the present invention provides a method of producing an IgG4 antibody with an improved colloidal stability, comprising introducing one or more modifications into the constant domains of IgG4, wherein said one or more modifications of one or more amino acid residues selected from the list consisting of R133, E137, D203, R214, E356, R409, E419 according to Kabat numbering.

Based on accumulated knowledge of several structures of antibodies, the following residues in the variable regions of IgG antibodies listed in Table 4a and Table 4b can be modified to improve the colloidal stability of an antibody. Hence in a particular embodiment of the methods of the present invention said one or more modifications are modifications of one or more amino acid residues selected from the list consisting of: residues 12, 18, 24, 39, 42, 45, 56 and 67 of the light chain and positions 13, 19, 64, 70, 75 and 83 of the heavy chain according to Kabat numbering.

TABLE 4a

Optimal framework positions in the light chain for charge modifications to reduce colloidal aggregation.

| Chain | Residue (Kabat) | Possibly forms H-bonds with other side chains | Common residues | Substitution |
|---|---|---|---|---|
| Light chain | 12 | Yes | Ser (may H-bond to Glu at position 105) | substitute with Asp or Glu to potentially form a salt bridge with Lys 107 and neutralize the positive charge |
| Light chain | 18 | Yes | Arg (may H-bond to Ser/Thr at position 20) | substitute with Ser, Thr or Gln to remove positive charge or substitute with Asp or Glu to introduce negative charge. |
| Light chain | 24 | Yes | Arg (may H-bond to one or more residues at positions 22, 69 and 70) | substitute with Ser, Thr or Gln to remove positive charge or substitute with Asp or Glu to introduce negative charge |
| Light chain | 39 | Yes | Lys (may H-bond to backbone carbonyl groups of positions 81 and 83, and to side-chains of residues at positions 81 and 168) | substitute with Ser, Thr or Gln to remove positive charge or substitute with Asp or Glu to introduce negative charge |
| Light chain | 42 | No | Lys or Gln | Lys: substitute with Ser, Thr or Gln to remove positive charge or substitute with Asp or Glu to introduce negative charge. Gln: substitute with Asp or Glu to introduce negative charge |
| Light chain | 45 | No | Lys or Arg | substitute with Ser, Thr or Gln to remove positive charge or substitute with Asp or Glu to introduce negative charge |
| Light chain | 56 | No | Ser | substitute with Asp or Glu to introduce negative charge |
| Light chain | 67 | No | Ser | substitute with Asp or Glu to introduce negative charge |

TABLE 4b

Optimal framework positions in the heavy chain for charge modifications to reduce colloidal aggregation.

| Chain | Residue (Kabat) | Possibly forms H-bonds with other side chains | Common residues | Substitution |
|---|---|---|---|---|
| Heavy chain | 13 | No | Lys or Gln | substitute with Ser, Thr or Gln to remove positive charge or substitute with Asp or Glu to introduce negative charge |
| Heavy chain | 19 | Possibly | Arg or Lys (although not clearly involved in H-bonding, Arg does pack against Tyr79) | substitute with Ser, Thr or Gln to remove positive charge or substitute with Asp or Glu to introduce negative charge. |
| Heavy chain | 64 | Yes | Lys or Gln (may be in a H-bond with residue at position 61 or carbonyl group of position 59) | substitute with Ser, Thr or Gln to remove positive charge or substitute with Asp or Glu to introduce negative charge |
| Heavy chain | 70 | No | Ser | substitute with Asp or Glu and potentially form a salt bridge with Lys/Arg at position 19 and neutralize the positive charge |
| Heavy chain | 75 | No | Lys | substitute with Ser, Thr or Gln to remove positive charge or substitute with Asp or Glu to introduce negative charge |
| Heavy chain | 83 | Yes | Arg (may H-bond to residue at position 86) | substitute with Ser, Thr or Gln to remove positive charge or substitute with Asp or Glu to introduce negative charge |

IgG Antibodies with an Improved Colloidal Stability

The present invention further provides a modified IgG1 or IgG4 antibody in which one or more charged amino acids of the constant region have been substituted by a polar (non-charged) amino acid. Such amino acids usually participate in hydrogen bonds as proton donors or acceptors. In particular a modified IgG1 antibody is provided in which one or more charged amino acids at positions K133, K214, H268, K274, R355, D356, K409 according to Kabat numbering have been substituted by a polar amino acid. Alternatively, the present invention provides a modified IgG4 antibody in which one or more charged amino acids at positions R133, E137, D203, R214, E356, R409, E419 according to Kabat numbering have been substituted by a polar amino acid. More specifically such polar amino acid is selected from the list consisting of Q, N, H, S, T, Y, C, and W. Such modified IgG1 or IgG4 antibodies exhibits better colloidal stability compared to unmodified antibody.

The present invention also provides a modified IgG1 antibody in which arginine (R) at position 355 according to Kabat numbering of the CH3 domain has been substituted with a polar amino acid. More specifically such polar amino acid is selected from the list consisting of Q, N, H, S, T, Y, C, and W. More particular such amino acid is glutamine (Q). More specifically such antibody exhibits better colloidal stability at pH7.4 compared to an unmodified IgG1. In particular the aggregation of the antibody is decreased at pH 7.4.

The present invention further provides modified IgG antibodies with an improved colloidal stability wherein one or more of the residues in the variable regions listed in Table 4a and Table 4b have been modified. Hence, the present invention provides a modified IgG antibody in which one or more amino acids at positions 12, 18, 24, 39, 42, 45, 56 and 67 of the light chain and positions 13, 19, 64, 70, 75 and 83 of the heavy chain according to Kabat numbering have been substituted by another amino acid to remove a positive charge or introduce a negative charge to minimize the charge sign difference between the domains of said IgG antibody.

Native state aggregation of the modified IgG antibodies can be measured using PEG 3350 solubility assay at a suitable pH, e.g. pH 7.4 or pH 5.0 (Wang et al 2014). Other measurements of native state aggregation include dynamic light scattering and size exclusion chromatography.

The modified IgG antibodies or other multidomain proteins with an improved stability obtainable using the methods disclosed herein can be produced using standard molecular biology techniques. Such methods are well-known to the skilled person. In one example the modified multi-domain protein is produced using an expression vector. Such expression vectors typically comprise a promoter operable in target cells used to overexpress the protein.

Method of Selecting and Producing Proteins with Improved Colloidal Stability

In yet another embodiment the present invention provides a method of selecting and producing one or more multi-domain proteins with improved colloidal stability, comprising obtaining two or more of multi-domain protein sequences from a panel of structurally similar multi-domain proteins sequences;

calculating for said two or more multi-domain protein sequences one or more charge scores for each of the domains;

selecting one or more multi-domain protein sequences from said two or more multi-domain protein sequences with the desired range of charge scores; and producing one or more multi-domain proteins using the selected multi-domain protein sequences.

More particular said one or more charge scores might be calculated for a subset of the domains. In particular sequences that have similar calculated charge for each domain or a subset of the domains are preferentially selected. More particular one or more multi-domain protein sequences are selected using the charge scores range that corresponds to lower charge difference between the oppositely charged domains of the proteins coded by such sequences.

In a particular embodiment the method additionally comprises:
calculating for each said two or more multi-domain protein sequences one or more hydrophobicity scores for each of the domains; and
selecting one or more multi-domain protein sequences with the desired range of the hydrophobicity scores.

In the first step of the method said one or more multi-domain protein sequences are selected from a set of sequences that share sequence identity. Such sequences might be variants of a multi-domain protein. Such sequences may differ from each other by one or more modifications to the amino acid sequence. Such structurally similar one or more multi-domain protein sequences can be a set of antibody sequences that have the same CDRs, but comprise one or more modifications to the constant regions. Such antibodies might also have the same CDRs while having a different isotype, particular a sub-set of sequences might be variants of IgG1 isotype and another subset of sequences might be variants of IgG4 isotype.

In one particular embodiment the charge score is calculated based on the count of the charged amino acids at the given pH. In yet another embodiment the charge score is calculated based on the count of the non-paired charged amino acids at the given pH. More specifically, the oppositely charged residues are located within a particular distance from each other are not taken into the determination of the charge score. More specifically such distance is less than 8, less than 7.5, less than 7, less than 6.5, less than 6, less than 5.5, or less than 5 Å. In a preferred embodiment such distance is less than 5 Å.

In a particular embodiment the one or more charge scores is a charge density score calculated for positively and negatively charged residues. More particular said score is weighted to the number of pairs of oppositely charged residues within a particular distance from each other. More specifically such distance is less than 8, less than 7.5, less than 7, less than 6.5, less than 6, less than 5.5, or less than 5 Å. In a preferred embodiment such distance is less than 5 Å.

In a particular embodiment the desired range of the charge scores corresponds to the sequences that have lower number of charged residues. Such score can be selected to take into account the number of charged residues. In particular the range is covering values below a selected threshold.

In a particular embodiment the desired range of the charge scores corresponds to the sequences that have lower number of unpaired charged residues. More particularly the desired range of the charge scores corresponds to the sequences that have lower number of unpaired charged residues and lower number of clusters of charged residues. Such clusters typically consist of multiple unpaired charged residues located in the close proximity from each other. In a particular embodiment the sequences having a charge score below pre-defined threshold are selected. More particular the one or more charge scores are calculated for the residues within the accessible surface area.

In a particular embodiment the one or more hydrophobicity scores is related to the hydrophobic accessible surface area. Such area can be established using the methods described above. In a specific embodiment the hydrophobic accessible surface area is defined by one or more hydrophobic residues selected from the list consisting of I, F, V, L, W, M, A, and G. In one embodiment the one or more hydrophobic scores are weighted to provide higher scores for hydrophobic residues within a particular distance from another hydrophobic residue. More specifically such distance is less than 8, less than 7.5, less than 7, less than 6.5, less than 6, less than 5.5, or less than 5 Å. In a preferred embodiment such distance is less than 5 Å. In a particular embodiment the desired range of the hydrophobicity scores corresponds to the sequences that have lower number of hydrophobic residues.

In a particular embodiment the desired range of the hydrophobic score corresponds to the sequences that have lower number of hydrophobic residues within a particular distance from another hydrophobic residue. More specifically such distance is less than 8, less than 7.5, less than 7, less than 6.5, less than 6, less than 5.5, or less than 5 Å.

In particular, Fv domains of IgG antibodies with >98 hydrophobic residues in the amino acid sequence is predicted to have a high probability to aggregate based on our experimental data. In this case the hydrophobic residue sum score is taken from the following set of hydrophobic residues present in the Fv domain: I+F+V+L+W+M+A+G. A Fv domain with <90 hydrophobic residues is expected to show a low propensity for native state aggregation based on our data, note electrostatic potential modulates the hydrophobic affect. These residue sum thresholds can be raised or lowered dependent on the required stringency.

In a particular embodiment the scores are calculated for the residues within the accessible surface area. In particular the accessible surface area can be determined using homology-based modeling using known 3D structures. More specifically the accessible surface area is determined using a 3D structure data, particular, using X-ray 3D structure data of said domain or said protein of interest.

In another embodiment the one or more hydrophobic and one or more charge scores can be combined to produce a combined score.

In an alternative embodiment the scores might be replaced by the counts of unpaired charged and hydrophobic residues as described herein. Hence, the present invention provides a method of selecting and producing one or more multi-domain proteins with an improved colloidal stability, comprising:
obtaining two or more multi-domain protein sequences from a panel of structurally similar multi-domain proteins sequences;
calculating for each said two or more multi-domain protein sequences the number of unpaired charged residues for each of the domains; and
selecting one or more multi-domain protein sequences from said two or more multi-domain protein sequences having minimal difference in number of unpaired charged residues between the domains;
and producing one or more multi-domain proteins using the selected one or more multi-domain proteins sequences.

In a particular embodiment said method additionally comprises:
calculating for each said two or more multi-domain protein sequences number of hydrophobic residues in the accessible surface area; and
selecting one or more multi-domain protein sequences with lower number of hydrophobic residues.

The modified versions of the proteins can be produced using an expression vector as described above.

Method of Screening for Multi-Domain Proteins with Improved Colloidal Stability

The present invention further provides a method of screening for multi-domain proteins with improved colloidal stability, comprising:
- selecting a multi-domain protein of interest;
- generating a set of sequences with one or more modifications to the charged amino acid residues of said protein to minimize the charge sign difference between the domains;
- calculating for each generated modified sequences a one or more charge scores for each of the domains of said protein at a given pH;
- selecting sequences with the desired range of the charge scores;
- producing multi-domain proteins using selected sequences;
- measuring the colloidal stability of the produced proteins; and
- identifying proteins with desired level of colloidal stability at the given pH.

In a particular embodiment the method additionally comprises:
- generating a set of sequences with one or more modifications to the highly hydrophobic residues to decrease the hydrophobicity of the domains;
- calculating for each generated modified sequences one or more hydrophobicity scores for each of the domains of said protein; and
- selecting sequences with desired range of the hydrophobicity scores.

In one particular embodiment the charge score is calculated based on the count of the charged amino acids at the given pH. In yet another embodiment the charge score is calculated based on the count of the non-paired charged amino acids at the given pH. More specifically, the oppositely charged residues are located within a particular distance from each other are not taken into the determination of the charge score. More specifically such distance is less than 8, less than 7.5, less than 7, less than 6.5, less than 6, less than 5.5, or less than 5 Å. In a preferred embodiment such distance is less than 5 Å.

In a particular embodiment the one or more charge scores is a charge density score calculated for positively and negatively charged residues. More particular said score is weighted to the number of pairs of oppositely charged residues within a particular distance from each other. More specifically such distance is less than 8, less than 7.5, less than 7, less than 6.5, less than 6, less than 5.5, or less than 5 Å. In a preferred embodiment such distance is less than 5 Å.

In a particular embodiment the desired range of the charge scores corresponds to the sequences that have lower number of charged residues. Such score can be selected to take into account the number of charged residues. In particular the range is covering values below a selected threshold.

In a particular embodiment the desired range of the charge scores corresponds to the sequences that have lower number of unpaired charged residues. More particularly the desired range of the charge scores corresponds to the sequences that have lower number of unpaired charged residues and lower number of clusters of charged residues. Such clusters typically consist of multiple unpaired charged residues located in the close proximity from each other. In a particular embodiment the sequences having a charge score below pre-defined threshold are selected. More particular the one or more charge scores are calculated for the residues within the accessible surface area.

In a particular embodiment the one or more hydrophobicity scores are related to the hydrophobic accessible surface area. Such area can be established using the methods described above. In a specific embodiment the hydrophobic accessible surface area is defined by one or more hydrophobic residues selected from the list consisting of F, I, W, L, V, M, A and G. In one embodiment the one or more hydrophobic scores are weighted to provide higher scores for hydrophobic residues within a particular distance from another hydrophobic residue. More specifically such distance is less than 8, less than 7.5, less than 7, less than 6.5, less than 6, less than 5.5, or less than 5 Å. In a preferred embodiment such distance is less than 5 Å. In a particular embodiment the desired range of the hydrophobicity scores corresponds to the sequences that have lower number of hydrophobic residues.

In a particular embodiment the desired range of the hydrophobic score corresponds to the sequences that have lower number of hydrophobic residues within a particular distance from another hydrophobic residue. More specifically such distance is less than 8, less than 7.5, less than 7, less than 6.5, less than 6, less than 5.5, or less than 5 Å. In a preferred embodiment such distance is less than 5 Å.

In a particular embodiment the scores are calculated for the residues within the accessible surface area. In particular the accessible surface area can be determined using homology-based modeling using known 3D structures. More specifically the accessible surface area is determined using a 3D structure data, particular, using X-ray 3D structure data of said domain or said protein of interest.

In another embodiment the one or more hydrophobic and one or more charge scores can be combined to produce a combined score.

The modified versions of said protein can be produced using an expression vector as described above.

Uses of the Multi-Domain Proteins with an Improved Colloidal Stability

The present invention further contemplates pharmaceutical compositions comprising a modified multi-domain protein with an improved colloidal stability in a mixture with a pharmaceutically acceptable excipient. The multi-domain proteins with an improved colloidal stability of the present invention can be also used in a form of pharmaceutical formulation.

System for Predicting Colloidal Stability

The present invention provides further a system for predicting colloidal stability of a multi-domain protein, said system comprising:
- a receiver configured to receive, one or more protein sequences;
- a charge score estimator configured to calculate the net charge per domain of said one or more protein sequences;
- a colloidal stability estimator configured to calculate one or more predictive stability scores at a given pH; and
- an output device configured to display the probability of colloidal stability calculated by the colloidal stability estimator.

More specifically the receiver is configured to receive one or more protein sequences via a network devise or via a user input device.

Optionally such system comprises an additional hydrophobicity estimator of the domains of said protein.

In a more specific embodiment the charge estimator outputs a score calculated based on the amino acid sequence. The hydrophobicity estimator outputs a score calculated based on the amino acid sequence.

In a particular embodiment the charge score at a given pH is determined by identifying charged residues in the accessible surface area, and wherein the opposite charged residues located within a particular distance from each other are not taken into the determination of the score. More specifically such distance is less than 8, less than 7.5, less than 7, less than 6.5, less than 6, less than 5.5, or less than 5 Å. In a preferred embodiment such distance is less than 5 Å.

More specifically the hydrophobicity score is calculated as described above in relation to the methods of the invention.

The present invention further provides a tangible computer-readable medium having stored thereon, computer-executable instructions that, if executed by a computing device, cause the computing device to perform a method for prediction of colloidal stability of a multi-domain protein comprising:
receiving one or more protein sequences;
calculating a charge score per domain of said sequences;
calculating one or more predictive colloidal stability scores at a given pH.

In particular the method comprises an additional step of estimating hydrophobicity of the domains of said sequences.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim.

The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

EXAMPLES

Example 1

Native State Colloidal Stability Measurement (PEG Aggregation Assay)

PEG-induced precipitation of the mAbs at 1 mg/mL was investigated in the presence of 7-20% PEG-3350 in PBS at pH 7.4 and 50 mM sodium acetate 125 mM sodium chloride pH 5.0. To minimize non-equilibrium precipitation, sample preparation consisted of mixing 2× protein and 2× PEG solutions at a 1:1 volume ratio in a 96 well v bottom plate. After mixing, samples were pre-incubated at 37° C. for 0.5 h to re-dissolve non-equilibrium aggregates. Samples were then incubated at room temperature for 24 h to reach equilibrium. The samples were subsequently centrifuged at 4000 g for 1 h at 20° C. Aliquots of the supernatants were immediately removed. A280 nm readings of the supernatant were taken using a FLUOstar Omega Multi-detection Microplate Reader (BMG LABTECH). Data points were plotted using Graphpad prism, PEG midpoints ($PEG_{mdpnt}$) were derived from sigmoidal dose-response (variable slope) fitting protocol.

Example 2

Mutant Generation

Mutations to the Fc fragment were introduced by site directed mutagenesis. Oligo's were designed to incorporate the desired mutations and ordered from Sigma. PCR reactions were set up to substitute amino acids using the Agilent Quikchange Lightning mutagenesis kits (Catalog #210518). Constructs were verified by sanger sequencing.

Transient Expression.

Heavy Chain and Light Chain plasmids were transfected into our in-house CHOSXE cell line using the ExpiCHO transfection system from Life technologies (Catalog Number A29133) ratio at a ratio of 1:2. Briefly, 100 ug DNA (total) were diluted in 4 ml Gibco OptiPRO Serum Free Media (SFM) (Thermofisher Catalog number: 12309019) and 320 ul Gibco ExpiFectamine CHO reagent (Catalog number A29129) was diluted in 4 ml OptiPRO SFM. The diluted DNA and transfection reagent was mixed and added to 100 ml cells seeded at $6\times10^6$ cells/ml. Cells were incubated on a shaking platform overnight at 37° C. On day 1 post transfection, feed and enhancer was added to the culture and the flasks were transferred to an incubator with the temperature set at 32° C. Transfections were cultured for 10 days after which the supernatant was harvested by centrifugation at 4000 RPM for 30 min to pellet the cells followed 0.22 µm sterile filtration.

Purification of Antibodies

Antibodies were purified using two-step purification process. A 5 ml MabSelect Sure column (catalog number 11003494, GE healthcare) and a S200 16/60 gel (catalog number 54802-U, GE healthcare) filtration column were attached to an Akta Xpress. The MabSelect Sure column was equilibrated in PBS pH7.4 and supernatant was applied at a flow rate of 5 ml/min. The column was washed with PBS pH7.4 and the bound material was eluted with 0.1 M Sodium Citrate, pH3.6. The eluted material was then applied to an S200 16/60 column (GE Healthcare) equilibrated into PBS, at a flow rate of 1 ml/min. 2 ml fractions were collected and appropriate fractions were pooled so that final samples had at least 95% purity.

Example 3

Calculation of pI

Calculation of pKa

There are three methods that can be used in the pKa calculations. The first method assumes that all Cysteines are forming Cystines. If there is an uneven number of cysteines in the sequence, a single Cysteine is assumed to be free. The second method assumes that half of the Cysteines present are participating in disulphide linkages (to form Cystine). The third method assumes that none of the Cysteines are participating in disulphide bonds.

The pKa values of different amino acids used for the calculations are shown in the table below

TABLE 5 pKa values of amino acids.

| Amino Acid Residue | pKa |
|---|---|
| N-terminus | 9.69 |
| Lysine | 10.5 |
| Arginine | 12.4 |
| Histidine | 6.0 |
| C-terminus | 2.34 |
| Aspartate | 3.86 |
| Glutamate | 4.25 |
| (Free) Cysteine | 8.33 |
| Tyrosine | 10.0 |

Calculation of pI

In order to calculate the pI, a net charge vs. pH plot is generated. The following steps are performed in order to create such plot.

Step 1: for each pH (from 1.0 to 14.0 in increments of 0.1), partial charge for each titratable residue is calculated. The pKa value used here depends on which method for pKa calculation is being used.

For N-terminus, His, Arg, and Lys: $Cp=1/(10^{(pH-pKa)}+1)$
For C-terminus, Asp, Glu, Cys, and Tyr: $Cp=1/(10^{(pH-pKa)}+1)-1$ Disulphide bonded cysteines do not contribute to this calculation.

Step 2: calculate the Net charge of the protein by taking the sum of all partial charges.

Step 3: generate the Net Charge vs. pH plot, then take the pI as the pH at which the net charge is closest to zero.

Example 4

Native State Colloidal Stability Analysis

To evaluate the PEG solubility assay as a useful indicator of native state colloidal stability three samples exhibiting low solubility (mAb16, mAb12, and mAb9) and three samples with high solubility (mAb2, mAb3 and mAb5) as determined by the PEG assay were concentrated and assayed for aggregates. Briefly the samples were filtered through a 0.22 μM filter to remove any particulate species that could potentially nucleate aggregation and buffer exchanged into PBS pH 7.4 or 50 mM acetate, 125 mM NaCl pH 5.0 using Sephadex PD-10 columns (GE Healthcare, catalog number 17-0851-01). Each sample was adjusted to 3.5 mg/mL, 2 mL of this solution was concentrated using centrifugal filter units (Amicon ultra-15 10K MWCO, catalog number Z706345), at 3000 g for 10 min or until the volume reached ~140 μL (~50 mg/mL). The concentrated fraction was recovered and promptly inspected for aggregation Immediately after concentration, mAb12 and mAb9 showed visible precipitation in both buffers, and became cloudy after 24 hour storage at 20° C. mAb16 showed visible precipitate, which increased with time forming an amorphous mass after 2 days. mAb2 mAb3 and mAb5 showed no evidence of aggregation over a two weeks incubation at 20° C. Additional validation was performed on several samples with a range of colloidal stabilities (data not shown), we observed no meaningful difference between the PEGmidpnt and observed aggregation propensity for all samples tested.

In addition to pI, the net charge of the Fab, variable region, CH1, Fc, CH2 and CH3 domains at pH 5.0 and pH 7.4 was calculated. FIG. 1 highlights charge differences between IgG1 and IgG4 constant domains.

The PEG solubility assay was used to determine the colloidal stability of thirty one humanized antibodies, (26 unique variable regions). The sample set contained thirteen IgG1 and eighteen IgG4 antibodies. A large range of solubility scores as defined by the PEG midpoint (PEGmdpt) was observed for both isotypes in PBS pH 7.4 and 50 mM sodium acetate, 125 mM sodium chloride pH 5.0.

Figure 2:
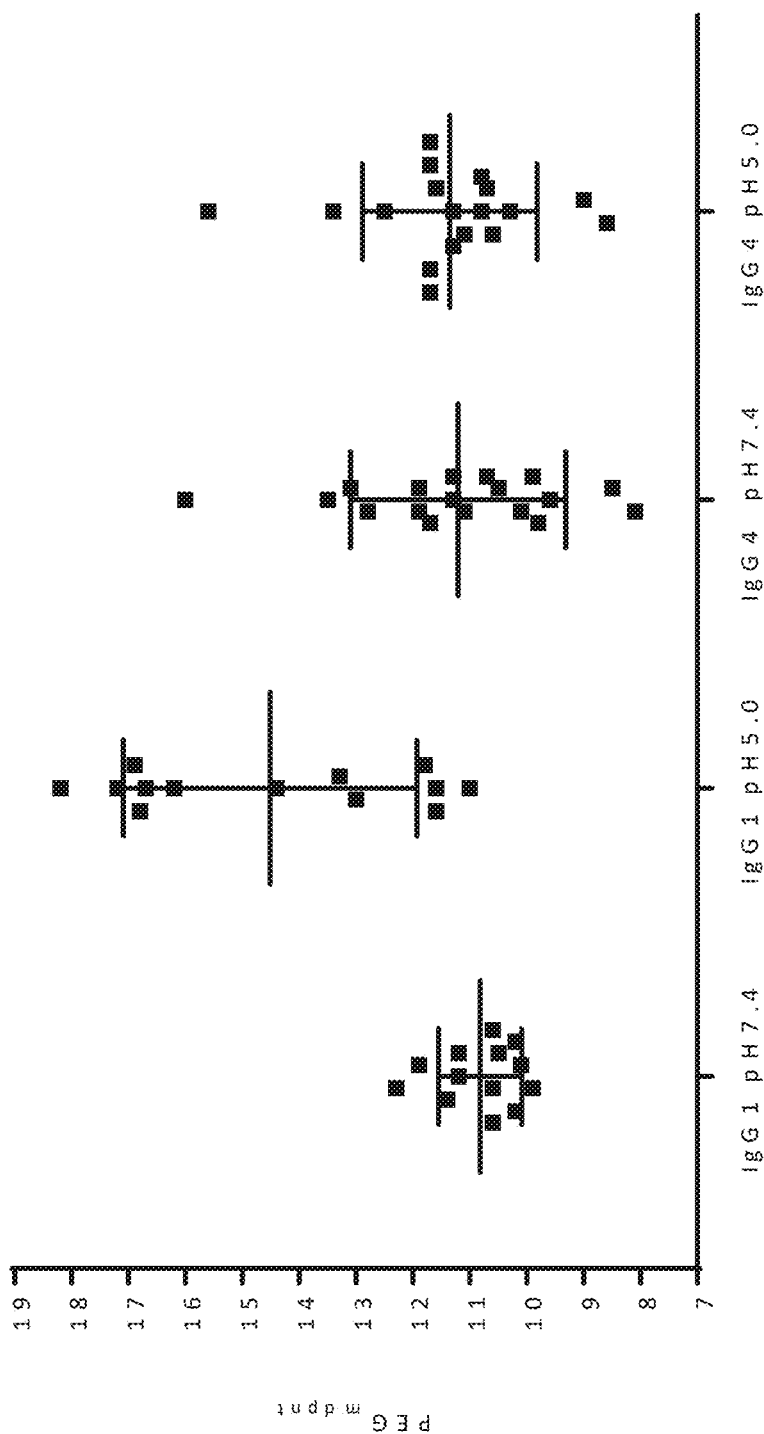
FIG. 2 plot of 13 IgG1 and 18 IgG4 humanised mAb PEGmdpnt values tested in PBS pH 7.4 and 50 mM sodium acetate, 125 mM NaCl pH 5.0. IgG1 sample set tend to show greater PEG midpoints at pH 5.0 compared to IgG1 sample set at pH 7.4. IgG4 sample set does not show significant solubility improvement at pH 5.0 compared to IgG4 sample set tested at pH 7.4.

A clear difference in isotype solubility is observed, IgG1 sample set show a statistically significant increase in solubility at pH 5.0 compared to the IgG4 sample set at pH 5.0. The IgG4 sample set have a broadly even distribution of colloidal stability scores in the buffers tested and are generally less prone to colloidal aggregation at pH 7.4 (FIG. 2).

Figure 3:
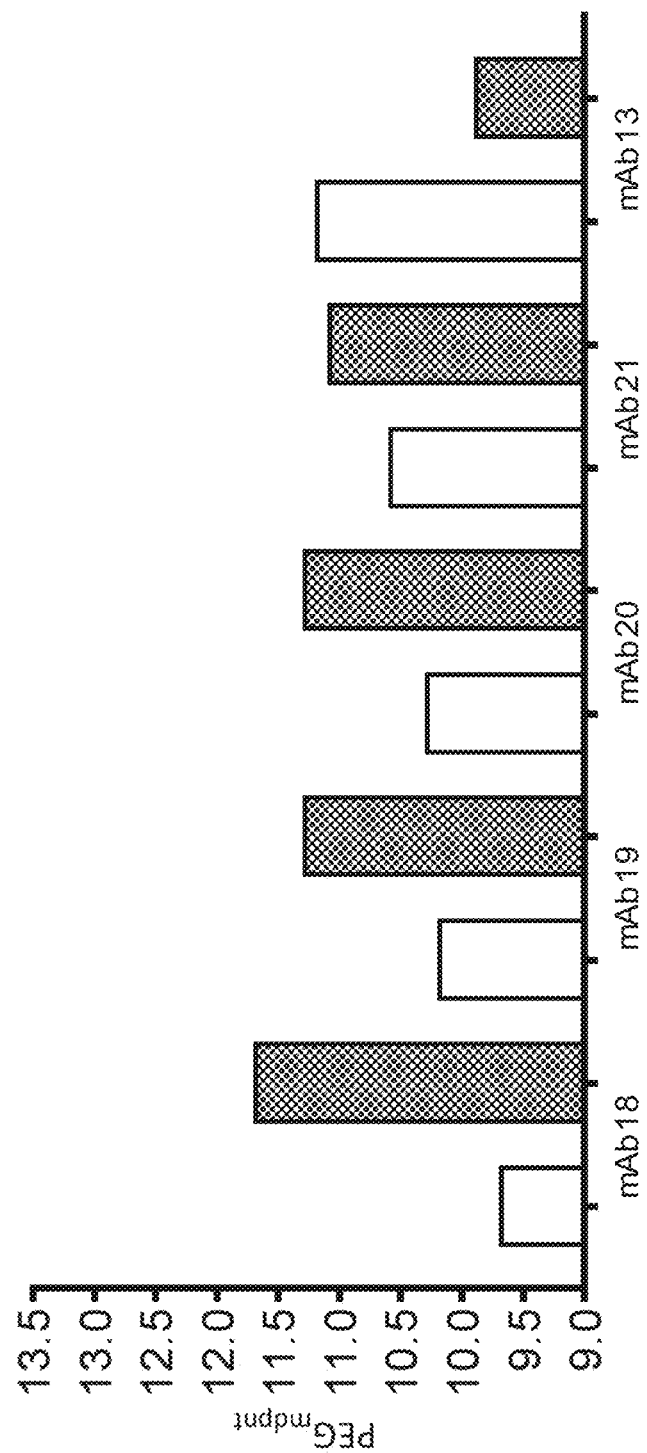
FIG. 3 shows six antibodies where variable regions were formatted as IgG4 (etched bars) and IgG1 (hollow bars) isotypes for analysis in the PEG 3350 solubility assay at pH 7.4.

The apparent solubility difference between the isotypes was investigated by comparing the solubility properties of variable regions generated as IgG1 and IgG4 isotypes. Five variable regions were formatted as IgG4 (etched bars) and IgG1 (hollow bars) isotypes for analysis in the PEG 3350 solubility assay at pH 7.4. Variable region domains with net negative charge or no overall charge exhibit greater colloidal stability as IgG4 mAbs. Conversely the variable region domain with high net positive charge exhibited greater colloidal stability as an IgG1 (FIG. 3 and Table 6).

TABLE 6

Fv net charge value
(number basic residues – number of acidic residues).

| Identifier | FV Calculated charge (pH 7.4) |
|---|---|
| mAb18 | −4 |
| mAb19 | −2 |
| mAb20 | −1 |
| mAb21 | 0 |
| mAb13 | 5 |

Figure 4A:
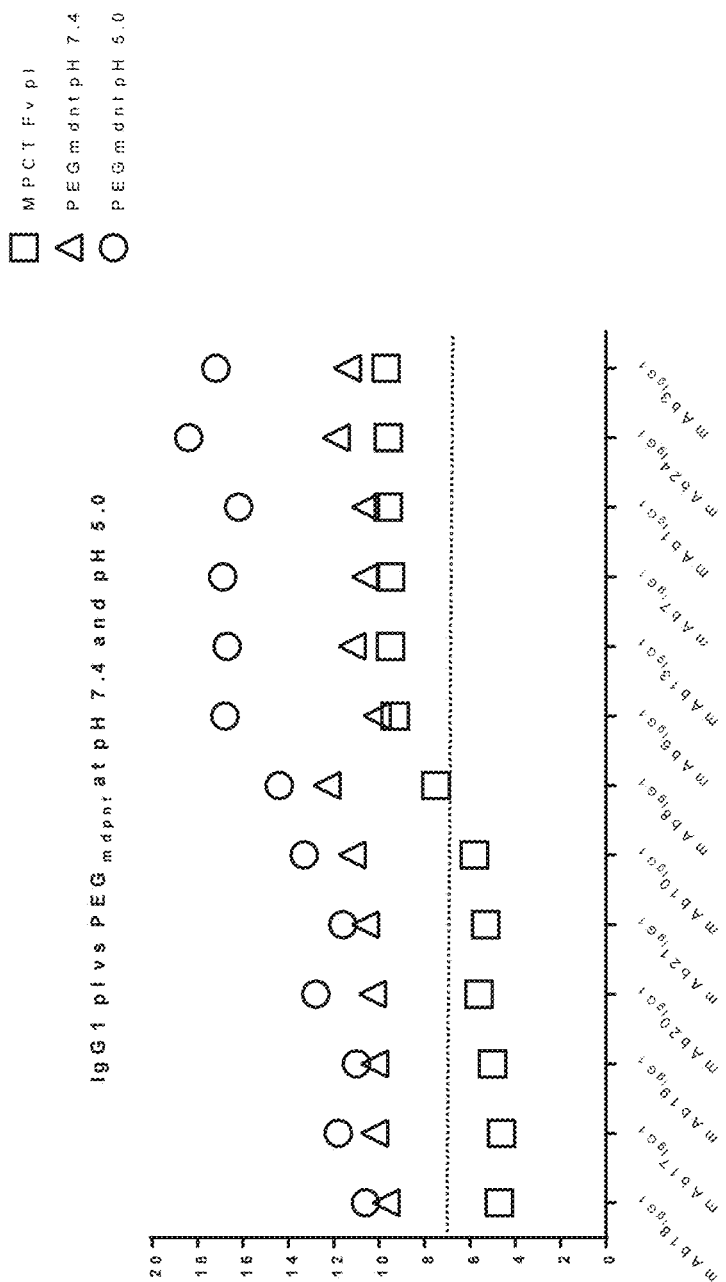
FIGS. 4a & 4b show plots of Fv domain pI values and PEGmdnt value at pH 7.4 and pH 5.0 for IgG1 and IgG4 samples. Squares represent calculated Fv domain pI values, triangles represent PEGmdpnt value at pH 7.4, and circles represent PEGmdnpt value at pH 5.0. Dashed line is a visual aid. Squares above the dashed line indicate positively charged Fv domains at pH 7.4, squares below the dashed line indicate negatively charged Fv domains at pH 7.4. The IgG1 mAb panel (FIG. 4a) shows improved PEGmdpnt scores at pH 5.0, the magnitude of improvement is substantial for Fv domains with fewer acidic residues (high pI). In contrast IgG4 mAbs (FIG. 4b) that possess Fv domains with fewer acidic residues (high pI) tend to show marginal improvements to PEGmdpnt scores at pH 5.0. It is notable that IgG4 mAb samples with a high number of acidic residues (low pI) tend to show similar or greater PEGmdpnt scores at pH 7.4 compared to the PEGmdpnt score at pH 5.0.

A comparison of PEGmdpnt values at pH 7.4 and pH 5.0 for the IgG1 panel shows improved PEGmdpnt scores at pH 5.0 for all of the IgG1 samples. Fv domains with net negative charge at pH 7.4 formatted as IgG1 mAbs exhibit modest improvements to solubility at pH 5.0 compared to the PEGmdpnt value measured at pH 7.4. Fv domains with net positive charge at pH 7.4 formatted as IgG1 mAbs exhibit greatly improved PEGmdpnt values at pH 5.0 compared to the PEGmdpnt value at pH 7.4 (FIG. 4a).

Figure 4B:
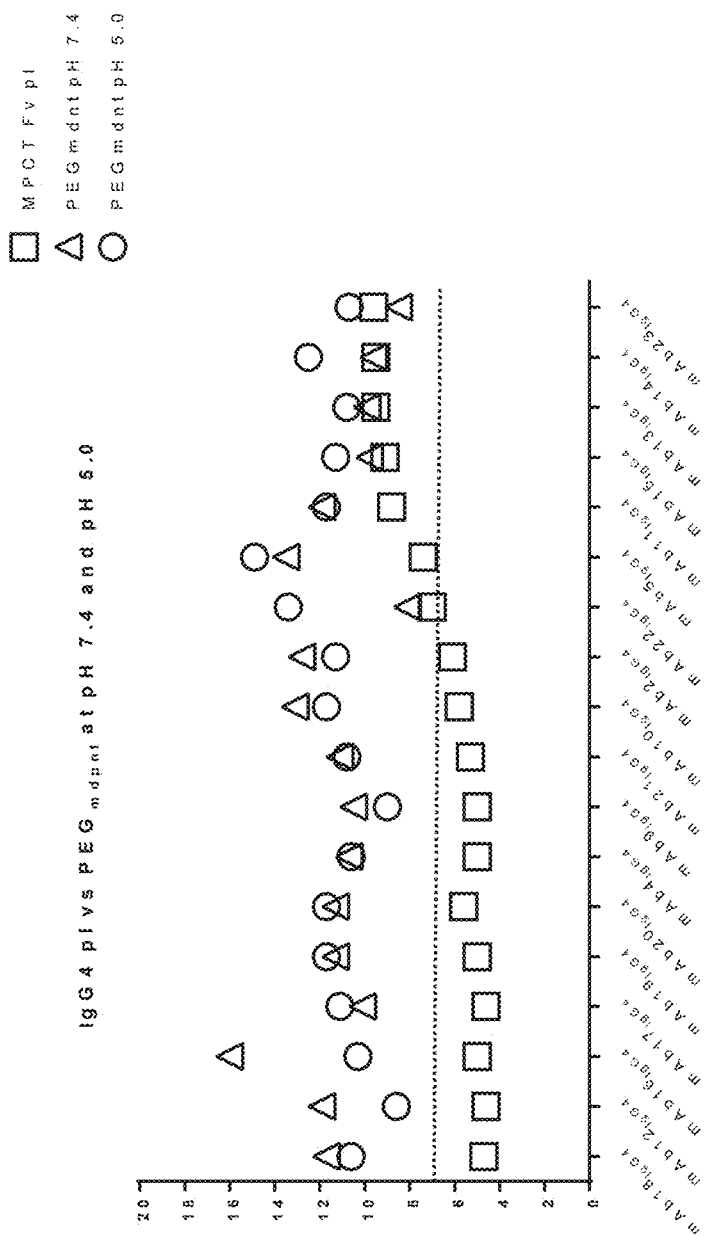
Figure 5:
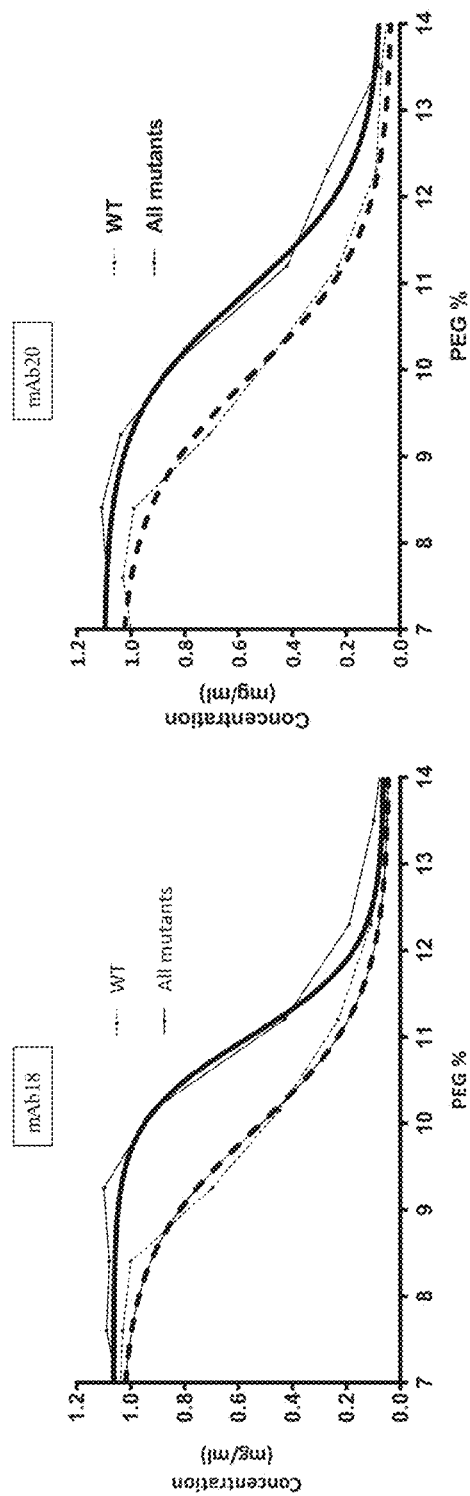
FIG. 5 shows PEG assay solubility plots of two unrelated IgG1 mAbs with IgG1 to IgG4 Fc charge mutants. Bold Dotted line indicates Wild Type (WT) fitted data; bold solid line indicates K274Q, R355Q, E419Q (all mutants combination).

In contrast to the IgG1 mAb panel, IgG4 mAbs with Fv domains that are negatively charged tend to show relatively high PEGmdpnts at pH 7.4 and exhibit lower (or similar) PEGmdpnt values at pH 5.0 compared to the PEGmdpnt value measured at pH 7.4. IgG4 samples that possess Fv domains with high pI values predominately show improved PEGmdpnt scores at pH 5.0 compared to the PEGmdpnt values at pH 7.4; however the PEGmdpnt gains are lower than is observed for IgG1 samples with positively charged Fv domains. It is notable that IgG4 mAbs with Fv domains possessing high pI values (low number of acidic residues) tend to show poor PEGmdpnt values at pH 7.4 (FIG. 4b).

IgG1 constant domains have net positive charge; IgG4 constant domains have net negative charge. We postulated that the increased probability of charge repulsion events was at least in part, responsible for the improved solubility for IgG4 samples (compared to the counterpoint IgG1 sample) with negatively charged variable domains. Following this logic, negatively charged variable regions paired with IgG1 isotypes increase the probability of attraction events. The increased probability of attractive forces would facilitate aggregation events resulting in poorer solubility relative to the IgG4 counterpart. The positively charged variable domain (mAb13) showed greater solubility as an IgG1 isotype compared to the IgG4 isotype (negatively charged Fc domain) fitting with the hypothesis.

IgG1 to IgG4 Fc charge mutations were introduced to two unrelated humanized IgG1 mAbs with negatively charged V regions possessing moderate to high levels of hydrophobicity (mAb 18 & mAb 20) to test the Fv constant domain charge interaction hypothesis. Four mutants of each parent mAb were generated; IgG1 KQ274, IgG1 R355Q, IgG1 Q419E and IgG1 K274Q R355Q Q419E (combined mutants) for analysis in the PEG solubility assay (FIG. 4 & Table 6). Both IgG1 samples containing the K274Q R355Q Q419E "combined mutants" show increased solubility. The single mutant IgG1 R355Q shows the greatest solubility increase for both samples. It is noteworthy that Q355 is adjacent to two negatively charged residues in the linear sequence, replacing Q with a positively residue could reduce the electrostatic potential of the two adjacent negatively charged residues. It is also important to note that the Q355R mutation is distal from Fcγ receptors binding, C1q binding, and FcRn binding sites.

In conclusion we have demonstrated that variable region net charge affects the aggregation propensity of IgG1 and IgG4 mAbs in a predictable manner This finding facilitates the generation of an improved aggregation prediction tool that takes into account domain interactions based on charge. Additionally we demonstrate solubility can be increased by swapping IgG constant domain residues with counterpoint IgG4 residues in rational manner based on the net charge sign of the variable region. If the biological function of the Fc domain is not a determining factor then solubility would be improved by selecting the isotype that has similar charge sign to the variable region.

TABLE 7

PEG midpoint values of IgG1 to IgG4 Fc charge mutants.

| ID | WT $PEG_{mdnt}$ | KQ $PEG_{mdnt}$ | RQ $PEG_{mdnt}$ | QE $PEG_{mdnt}$ | KQ, RQ, QE $PEG_{mdnt}$ |
|---|---|---|---|---|---|
| mAb18 | 9.9 | 10.2 | 10.7 | 10.2 | 11.0 |
| mAb20 | 10 | 10 | 10.6 | 10.1 | 10.8 |

Example 5

Isoelectric Point (pI) Measurement

A iCE3 whole-capillary imaged capillary isoelectric focusing (cIEF) system (ProteinSimple) can be used to experimentally determine pI.

Samples were prepared by mixing the following: 30 µL sample (from a 1 mg/mL stock in HPLC grade water), 35 µL of 1% methylcellulose solution (ProteinSimple), 4 µL pH 3-10 ampholytes (Pharmalyte), 0.5 µL of 4.65, 0.5 µl 9.77 synthetic pI markers (ProteinSimple), and 12.5 µL of 8 M urea solution (MERK). HPLC grade water was used to make up the final volume to 100 µl. The mixture was vortexed briefly to ensure complete mixing and centrifuged to remove air bubbles prior to analysis. Samples were focused for 1 min at 1.5 kV, followed by 5 min at 3 kV, 280 nm images of the capillary were taken using the Protein Simple software. The resulting electropherograms were analyzed using iCE3 software and pI values were assigned (linear relationship between the pI markers). The calibrated electropherograms were then integrated using Empower software (Waters).

Example 6

Ranking Hydrophobicity Using Hydrophobic Interaction Chromatography (HIC)

A Dionex ProPac HIC-10 column 100 mm×4.6 mm (ThermoFisher scientific) can be used to rank apparent hydrophobicity.

All separations are carried out on an Agilent HP1260 HPLC (Agilent) equipped with a fluorescence detector. The column temperature is maintained at 20° C. throughout the run, flow rate was set at 0.8 mL/min. The mobile phase for the HIC method consisted of 0.8 M ammonium sulfate, 50 mM phosphate pH 7.4 or 0.8 M ammonium sulfate, 50 mM sodium acetate pH 5.0 (buffer A) and 50 mM phosphate pH 7.4 or 50 mM sodium acetate pH 5.0 (buffer B). Following a 5 min hold at 0% B, bound protein is eluted using a linear gradient from 0 to 100% B over 45 min and the column is washed with 100% B for 2 min and re-equilibrated in 0% B for 10 min. The separation is monitored by intrinsic fluorescence with excitation occurring at 280 nm and emission at 340 nm.

Example 7

Fluorescence Based Thermal Stability (Tm) Measurement

A thermal stability assay can be used to assess conformational stability of purified molecules.

The reaction mix contained 5 µL of 30× SYPRO™ Orange Protein Gel Stain (Thermofisher scientific), diluted from 5000× concentrate with test buffer. 45 µL of sample at 0.2 mg/mL, in PBS pH 7.4, or 50 mM sodium acetate 125 mM sodium chloride pH 5.0, was added to the dye and mixed, 10 µL of this solution was dispensed in quadruplicate into a 384 PCR optical well plate and was run on a QuantStudio Real-Time PCR System (Thermofisher). The PCR system heating device was set at 20° C. and increased to 99° C. at a rate of 1.1° C./min. A charge-coupled device monitored fluorescence changes in the wells. Fluorescence intensity increases were plotted, the inflection point of the slope(s) was used to generate apparent midpoint temperatures (Tm). Domain assignments were made by reference to the known Tm's of the CH2 and CH3 domains in each test buffer.

Example 8

Native State Aggregation Analysis of WT and Charge Variants

The following framework (FW) amino acid residue substitution strategy was used. The predictions were based on an IgG4P mAb with a positively charged Fv domain at pH 7.4. The IgG4P mAbs contained a S241P mutation in the hinge region to reduce formation of half antibody associated with the IgG4 isotype. All samples contained Kappa light chains. Residue substitutions were introduced by site directed mutagenesis. Oligonucleotides were designed to substitute the desired residues (Sigma, UK). PCR reactions were set up to substitute bases using QuikChange Lightning Multi Site-Directed Mutagenesis Kit (Agilent). DNA constructs were verified by Sanger sequencing.

Two IgG4P mAbs were selected with positively charged Fv domains for analysis, mAbX$_{IgG4P}$ and mAbY$_{IgG4P}$ (+5 and +6 respectively at pH 7.4), each having a unique Fv domain that bind different ligands. Residue substitutions were introduced to the FWs, each replacement residue was chosen from a series of naturally occurring human residues at the selected positions as listed by the abYsis database. To minimize the risk of introducing destabilizing FW residue substitutions, only surface exposed residues, where the side-chain was not observed to H-bond to other side chains, were selected.

PEG$_{mdpnt}$ scores at pH 7.4 compared to WT as predicted. FW variant M3 (four neutral to negative residue substitutions) resulted in a comparatively modest improvement to PEG$_{mdnt}$ score for both mAbs. The M4 variant (four positive to negative residue substitutions) had a greater beneficial effect for mAbX$_{IgG4P}$. This was attributed to the greater net positive charge of mAbY$_{IgG4P}$. The introduction of negatively charged residues to the FW increases the relative probability of electrostatic attraction events due to comparatively high number of positively charged residues of mAbY$_{IgG4P}$. The M5 variant (four positive to neutral residue substitutions) resulted in a substantial increase in PEG$_{mdnt}$ score for both molecules.

A comparison of PEG$_{mdnpt}$ scores for mAbXIgG4P and mAbYIgG4P measured at pH 5.0 revealed significant differences in aggregation scores. WT PEG$_{mdpnt}$ score was increased for both mAbs as expected at pH 5.0 due to a greater probability of charge repulsion events caused by the larger number of positively charged residues at this slightly acidic pH. M3 showed a similar PEG$_{mdpnt}$ score at pH 5.0

TABLE 8

Summary of Framework (FW) residue substitutions introduced to mAbX$_{IgG4P}$ and mAbY$_{IgG4P}$.

| mAb | Substitution Type ID | Location | Substitution | Predicted effect | Heavy Chain | Light Chain |
|---|---|---|---|---|---|---|
| X | M3 | FW | Neutral to negative | Predicted to show reduced aggregation at pH 7.4 but greater aggregation at pH 5.0 | S70E | S12E, S56E, S67E |
| Y | | | | | | |
| X | M4 | FW | Positive to negative | Predicted to show reduced aggregation at pH 7.4 but greater aggregation at pH 5.0 | K64E, K75E | R18E, K42E |
| Y | | | | | | |
| X | M5 | FW | Positive to neutral | Predicted to show reduced native state aggregation at pH 7.4 and pH 5.0 | K64Q, K75S | R18S, K42Q |
| Y | | | | | | |

Thermal stability data indicated that all the samples were folded and comparable to WT, and that the molecules had thermal stabilities comparable to commercially available mAb therapeutics. Residue substitutions in the FW regions resulted in relatively minor affinity differences compared to WT and pH 7.4 for mAbX$_{IgG4P}$ and a slightly decreased PEG$_{mdpnt}$ score for mAbY$_{IgG4P}$. M4 showed a decrease in PEG$_{mdpnt}$ scores at pH 5.0. The substitution of positively charged residues with negatively charged residues resulted in a greater probability of electrostatic attractions at pH 5.0 as predicted. Again, mAbY$_{IgG4P}$ showed the largest

TABLE 9

Summary of pI, thermal stability and Biacore analyses for mAbX$_{IgG4P}$ and mAbY$_{IgG4P}$ with and without residue substitutions.

| | Calculated pI | | Calculated charge pH 7.4 | | Calculated charge pH 5.0 | | Fab domain Tm (° C.) | | Biacore (KD µM) | |
|---|---|---|---|---|---|---|---|---|---|---|
| | mAbX | mAbY | mAbX | mAbY | mAbX | mAbY | mAbX | mAbY | mAbX | mAbY |
| WT | 9.0 | 9.1 | 5 | 6 | 5 | 9 | 78.2 ± 0.1 | 74.2 ± 0.1 | 7.6 | 0.71 |
| M3 | 7.7 | 8.4 | 1 | 2 | 1 | 5 | 77.7 ± 0.1 | 74.1 ± 0.1 | 11.3 | 1.41 |
| M4 | 6.2 | 6.5 | −3 | −2 | −3 | 1 | 77.6 ± 0.1 | 72.5 ± 0.1 | 6.5 | 1.01 |
| M5 | 7.7 | 8.4 | 1 | 2 | 1 | 5 | 77.2 ± 0.1 | 76.2 ± 0.1 | 7.4 | 0.96 |

Figure 6:
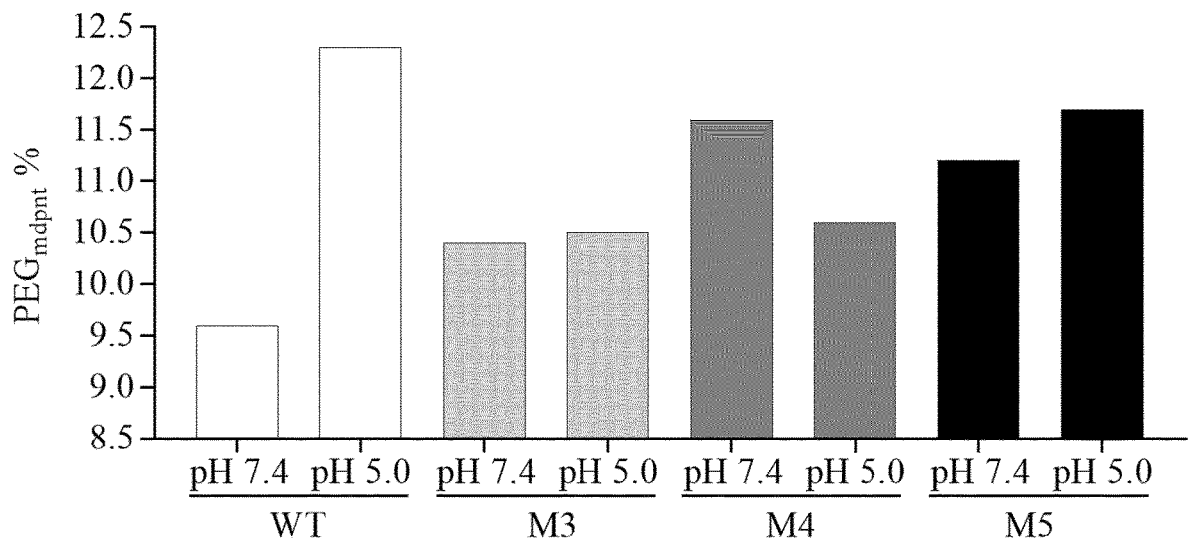
FIG. 6 shows a bar chart of $PEG_{mdpnt}$ scores for $mAbX_{IgG4P}$ WT/FW substitutions (A) and $mAbY_{IgG4P}$ WT/FW substitutions (B). The first and second bar within each group shows samples analyzed at pH 7.4 and pH 5.0 respectively.
Figure 6:
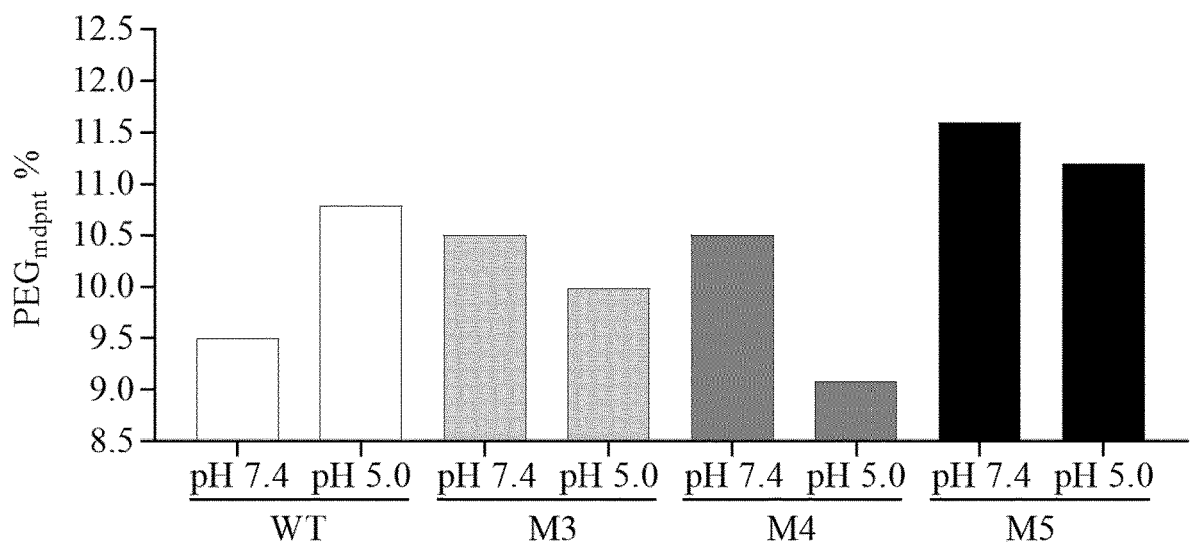

The PEG aggregation assay as described herein was used to determine native state aggregation propensity of mAbX$_{IgG4P}$ and mAbY$_{IgG4P}$ wild-type (WT) and charge variants (see FIG. 6). All the substitutions improved the decrease. Substituting positive framework residues with neutral residues (M5) resulted in an increased PEG$_{mdpnt}$ score compared to WT at pH 7.4 for both test mAbs, and decreased aggregation propensity at pH 5.0.

All the substitutions improved the $PEG_{mdpnt}$ scores at pH 7.4 compared to the WT mAbs as predicted. The removal of positively charged residues rather than the introduction of negatively charged residues tended to show greater $PEG_{mdpnt}$ improvement. This suggested that electrostatic repulsion had a relatively small effect and/or the addition of charged residues permits a greater number of unfavorable electrostatic interactions. The aggregation behavior at pH 5.0 for each variant was also consistent with our charged based native state aggregation model. At slightly acidic pH there was a substantial increase in positive charge due to the protonation of histidine residues. This resulted in an improved $PEG_{mdpnt}$ score for each WT sample as expected due to a greater probability of electrostatic repulsion events. The difference in magnitude of improvement at pH 5.0 for the two WT samples could be attributed to the number of histidine residues in the FW. Sequence analysis revealed that $mAbY_{IgGF4P}$ had three histidine residues in the Fv domain, $mAbX_{IgG4P}$ had none. It is plausible that these residues increase the probability of unfavorable intermolecular electrostatic interactions for $mAbY_{IgGF4P}$.

Substitution of neutral FW residues with negatively charged residues resulted (M3) in a similar or slightly lower $PEG_{mdnt}$ at pH 5.0 compared to the pH 7.4 result. This is explained by a greater probability of charge attraction events due to the increased number of negatively charged residues in the FW. The greater number of positively charged residues of $mAbY_{IgG4P}$ would increase the frequency of electrostatic interactions which could explain the decreased $PEG_{mdpnt}$ score relative to the pH 7.4 score. Substituting positively charged residues with negatively charged residues (M4) resulted in markedly lower $PEG_{mdpnt}$ scores at pH 5.0. This outcome was expected, as these residue substitutions simultaneously increase the probability of intermolecular electrostatic attraction events whilst decreasing the probability of intermolecular repulsion events. Substituting positive FW residues with neutral residues (M5) resulted in greatly increased $PEG_{mdnt}$ scores at both pH 7.4 and pH 5.0 for each sample compared to their respective WT. Counter to the improvement at pH 5.0 observed for $mAbX_{IgG4P}$ M5 there was a slight decrease in $PEG_{mdpnt}$ score for $mAbY_{IgG4P}$ M5 relative to the pH 7.4 M5 $PEG_{mdpnt}$ score. This is probably due to the three histidine residues in the FW region of $mAbY_{IgG4P}$ resulting in a greater likelihood of intermolecular electrostatic attractions compared to $mAbY_{IgG4P}$.

We applied our residue substitution strategy to several positively charged residues in the complementarity-determining region (CDR) of $mAbX_{IgG4P}$ and $mAbY_{IgG4P}$. The observed aggregation behaviors were consistent with the FW charge variants. However, as might be expected, the residue substitutions ablated affinity. Nevertheless, this would be a viable strategy for mAbs with known paratopes, or for curated affinity maturation.

In summary, the data demonstrates that the rationally designed residue substitutions following the methods described herein reduced the pI and decreased native state aggregation for all the test molecules at pH 7.4.

Example 9

Biacore Affinity Assay

For $mAbX_{IgG4P}$ as described in Example 8, the assay format was capture of mAb by immobilized anti-human IgG Fc followed by titration of ligand over the captured surface. Biomolecular interaction analysis using surface plasmon resonance technology (SPR) was performed on a Biacore T200 system (GE Healthcare Bio-Sciences AB). Affinipure F(ab')2 fragment goat anti-human IgG, Fc fragment specific (Jackson ImmunoResearch Lab, Inc.) in 10 mM sodium acetate, pH 5.0 buffer was immobilized on a CM5 Sensor Chip (GE Healthcare Bio-Sciences AB) via amine coupling chemistry to a level of approximately 5000 response units (RU) using HBS-EP+, (10 mM HEPES pH7.4, 150 mM NaCl, 3 mM EDTA, 0.05% (v/v) Surfactant P20, GE Healthcare Bio-Sciences AB) as the running buffer. Samples were diluted to between 0.6 and 0.8 µg/mL in running buffer. A 60 s injection of mAb at 10 µL/min was used for capture by the immobilized anti-human IgG Fc to give a capture level of approximately 150 RU. Ligand was titrated from 40 µM to 0.62 µM over the captured mAb for 60 s at 30 µL/min followed by 60 s dissociation. The surface was regenerated by injections of 40 mM HCl for 60 s, 5 mM NaOH for 30 s and 40 mM HCl for 30 s at 10 µL/min. The data was analyzed using Biacore T200 evaluation software (version 3.0). Steady state fitting was used to determine affinity values.

For $mAbY_{IgG4P}$ as described in Example 8, the assay format was titration of $mAbY_{IgG4P}$ over the immobilized ligand. The ligand was prepared in 10 mM NaAc, pH 3.5, and immobilized on flow cell surfaces of a CM5 Sensor Chip via amine coupling chemistry to reach an immobilization level of approximately 40 RU. The running buffer was HBS-EP+, pH7.4 and $mAbY_{IgG4P}$ was injected at 7 concentrations from 0.05 nM to 200 nM over the immobilized ligand surfaces with a contact time of 3 mins and disassociation time of 30 mins, at a flow rate of 100 µL/min. The surface was regenerated by 2 injections of 50 mM HCl, for 90 s and 60 s respectively at a flow rate of 10 µL/min. The data were analyzed using the Biacore T200 evaluation software (version 3.0) using the bivalent analyte model with assumed no bulk contribution (RI=0) and global Rmax.

REFERENCES

Banks et al (2012) J. Pharm. Sci. 101, 2720-2732.
Black and Mould (1991) Anal Biochem.; 93(1):72-82.
Chothia and Lesk (1987) J. Mol. Biol. 196:901-917
Daniels and Alberty (1961) "Physical Chemistry", Second Edition, John Wiley and Sons, Inc., pages 364, 365, 428-430
Eisenberg and McLachlan (1986) Nature;319(6050):199-203.
Gibson et al (2011) J. Pharm. Sci. 100, 1009-1021.
Hessa et al (2005) Nature.;433(7024):377-81.
Kabat et al. (1991), SEQUENCES OF PROTEINS OF IMMUNOLOGICAL INTEREST, 5th Ed. Public Health Service, National Institutes of Health, Bethesda, Md.
Kyte and Doolittle (1982) J Mol Biol.;157(1):105-32.
Leem et al (2016) MAbs. 8(7):1259-1268. Epub 2016 Jul. 8.
Monera et al. (1995) J. Protein Sci.; 1: 319-329
Wang et al (2014) Mol Pharmaceutics; 11: 1391-1402
Wimley and White (1996) Nat Struct Biol; 3(10):842-8.

What is claimed is:

1. A method of producing an IgG4 antibody with an improved colloidal stability comprising:
    calculating for each domain of said IgG4 antibody the total net charge at a given pH;
    modifying the DNA sequence encoding the IgG4 antibody to introduce one or more modifications to the amino acid residues of the constant region of said IgG4 antibody to minimize the charge sign difference between the domains, wherein said one or more modification is, or each are, a substitution of a charged amino acid by a polar, non-charged amino acid, wherein said one or more modifications is, or are, selected from the list consisting of residues at positions R133, E137, D203, R214, E356, R409, E419 of Fc domain; and producing the IgG4 antibody with improved colloidal stability at the given pH.

2. The method of claim 1 additionally comprising:

calculating the hydrophobicity of the domains of said IgG4 antibody;

modifying the DNA sequence encoding the IgG4 antibody to introduce one or more modifications to the hydrophobic residues to decrease the hydrophobicity of the domains; or calculating for each domain of said IgG4 antibody of interest the number of unpaired charged amino acid residues.

3. The method of claim 1, wherein the one or more modifications: minimize the number of charged residues.

4. The method of claim 1, wherein the total net charge at a given pH is calculated by identifying opposite charged residues in the accessible surface area, and wherein the opposite charged residues located within a distance of less than 8 Å from each other are not taken into the determination of the total charge.

5. The method of claim 4, wherein said distance is less than 5 Å.

6. The method of claim 5, wherein the total net charge is the sum of unpaired charged residues.

7. The method of claim 1, wherein said IgG4 antibody is produced using an expression vector.

8. The method of claim 1, wherein colloidal stability is measured using a PEG induced precipitation assay.

9. The method of claim 1, wherein one or more of the domains are not modified.

10. A method of producing an IgG1 or IgG4 antibody with an improved colloidal stability comprising:

calculating for each domain of said IgG1 or IgG4 antibody the total net charge at a given pH;

modifying the DNA sequence encoding the IgG1 or IgG4 antibody to introduce one or more modifications to the amino acid residues of the constant region of said IgG1 or IgG4 antibody to minimize the charge sign difference between the domains, wherein said one or more modification is, or each are, a substitution of a charged amino acid by a polar, non-charged amino acid;

modifying the DNA sequence encoding the IgG1 or IgG4 antibody to substitute one or more amino acids at positions 12, 18, 24, 39, 42, 45, 56 and 67 of the light chain and positions 13, 19, 64, 70, 75 and 83 of the heavy chain according to Kabat numbering by another amino acid to remove a positive charge or introduce a negative charge to minimize the charge sign difference between the domains of said IgG1 or IgG4 antibody; and producing the IgG1 or IgG4 antibody with an improved colloidal stability at the given pH.

11. The method of claim 10 additionally comprising:

calculating the hydrophobicity of the domains of said IgG4 antibody;

modifying the DNA sequence encoding the IgG1 or IgG4 antibody to introduce one or more modifications to the hydrophobic residues to decrease the hydrophobicity of the domains; or calculating for each domain of said IgG4 antibody of interest the number of unpaired charged amino acid residues.

12. The method of claim 10, wherein the one or more modifications: minimize the number of charged residues.

13. The method of claim 10, wherein the total net charge at a given pH is calculated by identifying charged residues in the accessible surface area, and wherein the opposite charged residues located within a distance of less than 8 Å from each other are not taken into the determination of the total charge.

14. The method of claim 13, wherein said distance is less than 5 Å.

15. The method of claim 14, wherein the total net charge is the sum of unpaired charged residues.

16. The method of claim 10, wherein said IgG1 or IgG4 antibody is produced using an expression vector.

17. The method of claim 10, wherein colloidal stability is measured using a PEG induced precipitation assay.

18. The method of claim 10, wherein one or more of the domains are not modified.

* * * * *